US012789004B2

(12) United States Patent
Huettemann et al.

(10) Patent No.: US 12,789,004 B2

(45) Date of Patent: Nov. 10, 2026

(54) SYSTEMS AND METHODS FOR TREATING ISCHEMIC-REPERFUSION AND OTHER INJURIES USING A WAVEGUIDE

(71) Applicants: Wayne State University, Detroit, MI (US); The Regents of the University of Michigan, Ann Arbor, MI (US); Mitovation, Inc., Ann Arbor, MI (US)

(72) Inventors: Maik Huettemann, Grosse Pointe Park, MI (US); Thomas Sanderson, Plymouth, MI (US); Thomas Waddell, New Brighton, MN (US); Sam Tuck, Superior Township, MI (US)

(73) Assignees: Wayne State University, Detroit, MI (US); The Regents of the University of Michigan, Ann Arbor, MI (US); Mitovation, Inc., Ann Arbor, MI (US)

( * ) Notice: Subject to any disclaimer, the term of this patent is extended or adjusted under 35 U.S.C. 154(b) by 262 days.

(21) Appl. No.: 18/580,965

(22) PCT Filed: Jul. 19, 2022

(86) PCT No.: PCT/US2022/037628

§ 371 (c)(1),
(2) Date: Jan. 19, 2024

(87) PCT Pub. No.: WO2023/003903

PCT Pub. Date: Jan. 26, 2023

(65) Prior Publication Data

US 2024/0374915 A1 Nov. 14, 2024

Related U.S. Application Data

(60) Provisional application No. 63/223,677, filed on Jul. 20, 2021.

(51) Int. Cl.
*A61N 5/06* (2006.01)
*A61N 5/00* (2006.01)

(52) U.S. Cl.
CPC ...... *A61N 5/0613* (2013.01); *A61N 2005/005* (2013.01); *A61N 2005/0626* (2013.01);
(Continued)

(58) Field of Classification Search
None
See application file for complete search history.

(56) References Cited

U.S. PATENT DOCUMENTS

2004/0100796 A1* 5/2004 Ward .................. G02B 6/0068 362/240
2004/0116985 A1 6/2004 Black
(Continued)

FOREIGN PATENT DOCUMENTS

JP 2019514517 A 6/2019
WO 2021108627 A1 6/2021

OTHER PUBLICATIONS

International Search report, PCT/US2022/037628, dated Oct. 10, 2022.

(Continued)

*Primary Examiner* — Jerry Rahll

(57) ABSTRACT

A near-infrared (NIR) light therapy device having at least one NIR light source and a waveguide having i) a NIR light input surface and ii) a NIR light emitting surface. The waveguide includes a lens feature forming the NIR light input surface. The lens feature is configured to at least substantially collimate treatment NIR light from the at least one NIR light source and convey substantially collimated light in a first direction through the waveguide. The waveguide also includes a plurality of extractive surfaces on a surface of the waveguide that is configured to reflect the
(Continued)

substantially collimated light through the light emitting surface to a subject. The plurality of extractive surfaces is also configured to create a substantially uniform NIR light output across the light emitting surface.

16 Claims, 22 Drawing Sheets

(52) U.S. Cl.
CPC .............................. *A61N 2005/063* (2013.01); *A61N 2005/0632* (2013.01); *A61N 2005/0647* (2013.01); *A61N 2005/065* (2013.01); *A61N 2005/0659* (2013.01); *A61N 2005/0664* (2013.01)

(56) References Cited

U.S. PATENT DOCUMENTS

2007/0150030 A1 6/2007 Pearl
2007/0179570 A1* 8/2007 De Taboada ........... A61H 7/006 607/88
2007/0208395 A1 9/2007 Leclerc
2007/0239232 A1* 10/2007 Kurtz ...................... G02B 6/001 607/87
2011/0213447 A1* 9/2011 Hottinger ............. A61B 18/203 607/90
2011/0216549 A1* 9/2011 Futami ................. B60Q 1/0041 362/520
2014/0104862 A1* 4/2014 Jeong ..................... F21S 43/245 362/511
2016/0033705 A1* 2/2016 Fattal ................... G02B 6/0031 359/462
2017/0304645 A1* 10/2017 Schomacker ............ A61N 1/40
2018/0128961 A1 5/2018 Lim
2019/0126061 A1* 5/2019 Hong ................... A61N 5/0617
2019/0344095 A1 11/2019 Landa
2021/0301994 A1* 9/2021 Juhanak ................ F21S 43/239
2023/0375770 A1* 11/2023 Araki ................... G02B 6/0038

OTHER PUBLICATIONS

Japanese Reasons for Rejection dated Feb. 3, 2026 for Japanese Patent Application No. 2024-503895.

* cited by examiner

SYSTEMS AND METHODS FOR TREATING ISCHEMIC-REPERFUSION AND OTHER INJURIES USING A WAVEGUIDE

CROSS-REFERENCE TO RELATED APPLICATIONS

This application is a US National Phase application of International Application No. PCT/US2022/037628, filed on Jul. 19, 2022, which_claims priority to U.S. Provisional Application No. 63/223,677 filed on Jul. 20, 2021, the contents of both of which are hereby incorporated by reference in their entirety.

GOVERNMENT LICENSE RIGHT

This invention was made with government support under NS105238 and NS120322 awarded by the National Institutes of Health. The government has certain rights in the invention.

TECHNICAL FIELD

In general, various embodiments of this invention relate to systems and methods for treating ischemic-reperfusion injury and, specifically, to a wearable device having light delivery units configured to deliver light energy to an injured body region (e.g., a head region) of a user.

BACKGROUND

Typically, the treatment of body tissue (e.g., subdermal body tissue) requires invasive forms of therapy, including surgical and pharmaceutical intervention. Near infrared (NIR) light has been shown to provide therapeutic treatment to body tissue suffering the effects of ischemia/reperfusion (IR) injury. Specifically, NIR light at wavelengths of approximately 750 nm and 940 nm have been effective treating the effects of IR injury by modulating mitochondrial activity of body tissue under oxidative stress. NIR light has been effective as a form of therapy due to body tissue's transparency to NIR light, as well as body fluid's low absorbency of NIR light.

While the therapeutic effects of NIR light treatments are clear, the practical delivery of NIR light to body tissue of patients can be challenging. Conventional NIR light therapy devices can apply unwanted pressure to a body region due to their rigid form. These devices often are comprised of inflexible materials that are unsuitable for use by a wide variety of patients (e.g., adults, children, infants, etc.). Even conventional NIR light therapy devices that can avoid applying unwanted pressure to a body region are often functionally ineffective, as they target superficial body tissue via low level light therapy. Furthermore, both types of these devices can cause patient discomfort and potential injury when they lack effective systems to mitigate heat generated through absorption of the NIR light by hair and other tissues at site of the region being treated. As a result, patients may face discomfort or even pain when using a conventional NIR light therapy device. Accordingly, a need exists for improved therapy devices that provide comfortable, adaptable NIR light therapy to patients.

SUMMARY

The invention is based, in part, upon the development of a waveguide for directing light, e.g., NIR light, safely and effectively into the tissue of a subject.

In one aspect, embodiments of the invention feature a waveguide for delivering light, e.g., NIR light, into the tissue of a subject. The waveguide includes a light entry portion; an extraction portion comprising a plurality of extraction features adapted to redirect light received from the light entry portion; and an emitting portion adapted to receive the light from the extraction portion and emit the light onto the tissue surface of the subject.

In various embodiments, the light entry portion includes an aspherical lens. The light entry portion can further include a light channel so that light entering the aspherical lens is dispersed and passes along the light channel to the extraction portion. In some embodiments, the plurality of extraction features include at least three extraction features. In some embodiments, at least one outer surface of the waveguide can further comprise reflective coating adjacent thereto. In some embodiments, a gap can be formed between the reflective coating at the plurality of extraction features. In some embodiments, the plurality of extraction features are adapted to redirect the light received from the light entry portion to a direction substantially perpendicular to the skin surface of the subject. Each of the plurality of extraction features can include a surface oriented at an angle with respect to the direction normal to the skin surface, where the angle is in a range from +20 degrees to 70 degrees (i.e., in a range from 20 degrees to 70 degrees in either a clockwise or counterclockwise direction with respect to the direction normal to the skin surface).

In some embodiments, the emitting portion includes a flat shape. In some embodiments, the emitting portion includes an arcuate shape comprising a concave lower surface, where the concave lower surface can be adapted to conform to the skin surface of the subject. The concave lower profile can include a radius of curvature in a range from 3 cm to 10 cm.

In some embodiments, the waveguide includes an integrated cooling system adapted to cool the skin surface of the subject. The integrated cooling system can be disposed within the emitting portion. The integrated cooling system can include a fluidic channel molded within the emitting portion and adapted to carry a coolant fluid (e.g., water). The fluidic channel can include a serpentine shape. The serpentine shape can be defined by a plurality of substantially parallel conduits each connected by a bend, wherein the diameter of the inner surface of the substantially parallel conduits is greater than the diameter of the inner surface of the bends. The fluidic channel can occupy at least 20 percent of a surface area of the emitting portion.

In some embodiments, at least a portion of the waveguide can be defined by a biocompatible, compliant material. The biocompatible, compliant material can be a silicone material (e.g., optically clear silicone), where the silicone material comprises an elastic modulus in a range from 1 MPa to 50 MPa. The tissue surface can include a skin surface.

In general, in another aspect, embodiments of the invention feature a light treatment device for delivering light to a skin surface of a subject. The light treatment device can include at least one waveguide as described herein and a support member adapted to retain at least one waveguide and position the at least one waveguide proximate the skin surface of the subject.

In various embodiments, the support member can retain an array of waveguides. The support member can include at least one of a strap, a cap, a helmet, or a combination thereof. The support member can be adapted to position at least one waveguide so as to avoid interaction between the emitted light and a predetermined region of the subject, where the predetermined region can include a venous sinus. In some embodiments, the light treatment device includes a temperature measurement system for determining a temperature of the skin surface of the subject. The temperature measurement system can include a first probe for measuring a temperature of coolant fluid entering the waveguide via an inlet of the fluidic channel; a second probe for measuring a temperature of the coolant fluid exiting the waveguide at an outlet of the fluidic channel; and a reference probe for measuring a skin temperature at a non-treated location of the subject.

In some embodiments, the light treatment device includes a light source for producing an d delivering the light to at least one waveguide, where the light source comprises at least one of a diode, a laser or a laser diode. The light source can produce light having wavelengths of about 750 nm or about 940 nm. In some embodiments, the light source can produce light having wavelengths of 750 nm±30 nm or about 940 nm±30 nm.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

The invention is based, in part, upon the development of a waveguide for directing light, e.g., NIR light, safely and effectively into the tissue of a subject. One or more of the waveguides can be incorporated into a light delivery unit to deliver the light into the tissue of the subject.

Light Delivery Unit (LDU)

Figure 1A:
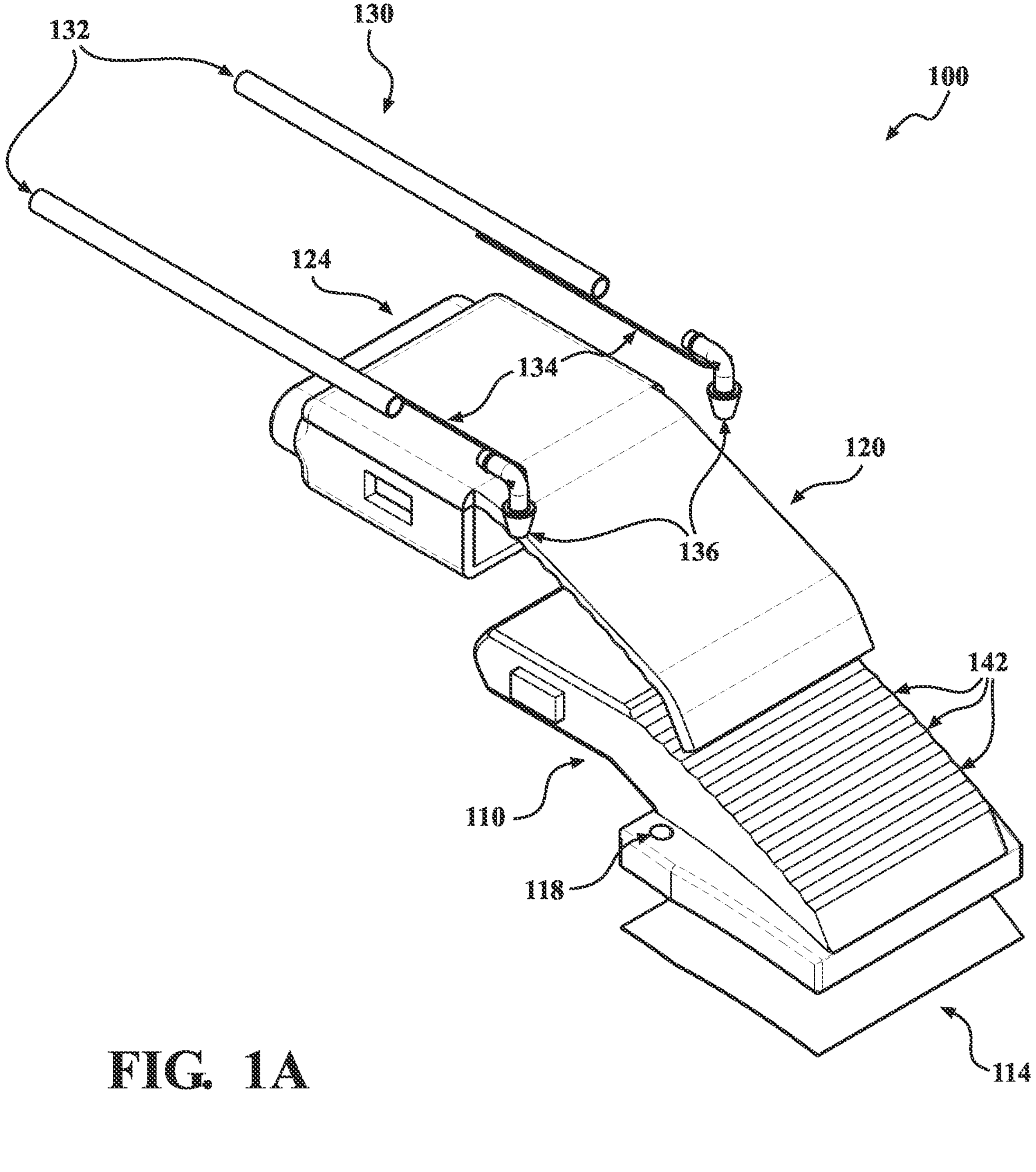
FIG. 1A is a schematic, perspective, exploded view of an example light delivery unit (LDU), according to various embodiments.

FIG. 1A is an exploded view of an exemplary light delivery unit (LDU) 100. The LDU 100 may include one or more components. In some cases, the LDU 100 may include a waveguide 110. The waveguide 110 may be configured to receive an optical (e.g., NIR light) input. The waveguide 110 may be configured to redirect the received optical input and emit an optical output via an emitting surface 114. For example, waveguide 110 may emit a redirected NIR light signal via the emitting surface 114 to a tissue surface of a user. In some cases, the waveguide 110 may include one or more extraction features 142 configured to redirect the received optical input as to be described herein.

In general, the waveguide 110 may be comprised of any suitable material(s) having the characteristics as described herein. In some cases, the waveguide 110 may be comprised of silicone. The silicone may be transparent and/or low durometer silicone. For example, the silicone may have a durometer in a range from 20 shore A to 80 shore A (e.g., 50 shore A). The silicone may be flexible and/or compressible, such that the waveguide 110 can conform to a surface (e.g., a skin surface) of the subject. In some cases, the silicone may comprise an elastic modulus in a range from 1 MPa to 50 MPa. In some cases, one or more faces or surfaces of the waveguide 110 may be covered with and/or otherwise coupled to a reflective material. In one embodiment, top faces, side faces, and one or more extraction features 142 of the waveguide 110 may include the reflective material. The reflective material may reflect one or more optical signals that are not redirected by the extraction features 142 (described below) such that they remain contained within the waveguide 110. The reflective material may improve extraction efficiency for redirection of one or more optical signals by the extraction feature(s).

Figure 1B:
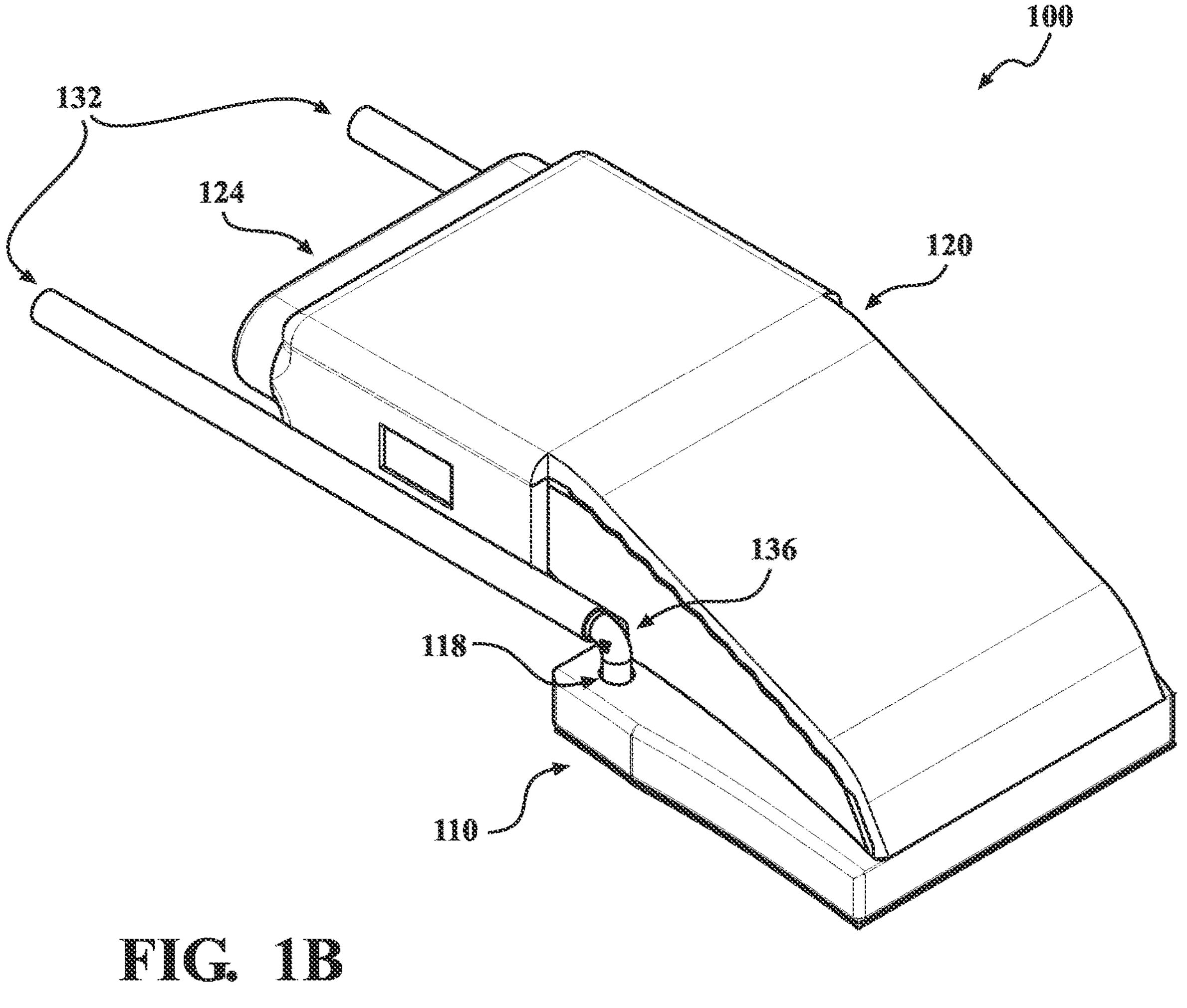
FIG. 1B is a schematic, perspective, assembled view of the example LDU of FIG. 1A.
Figure 1C:
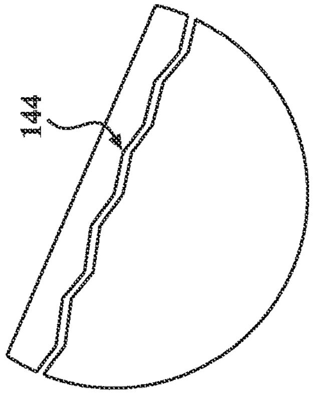
FIG. 1C is a schematic, side, enlarged view of the example LDU of FIG. 1A.
Figure 1C:
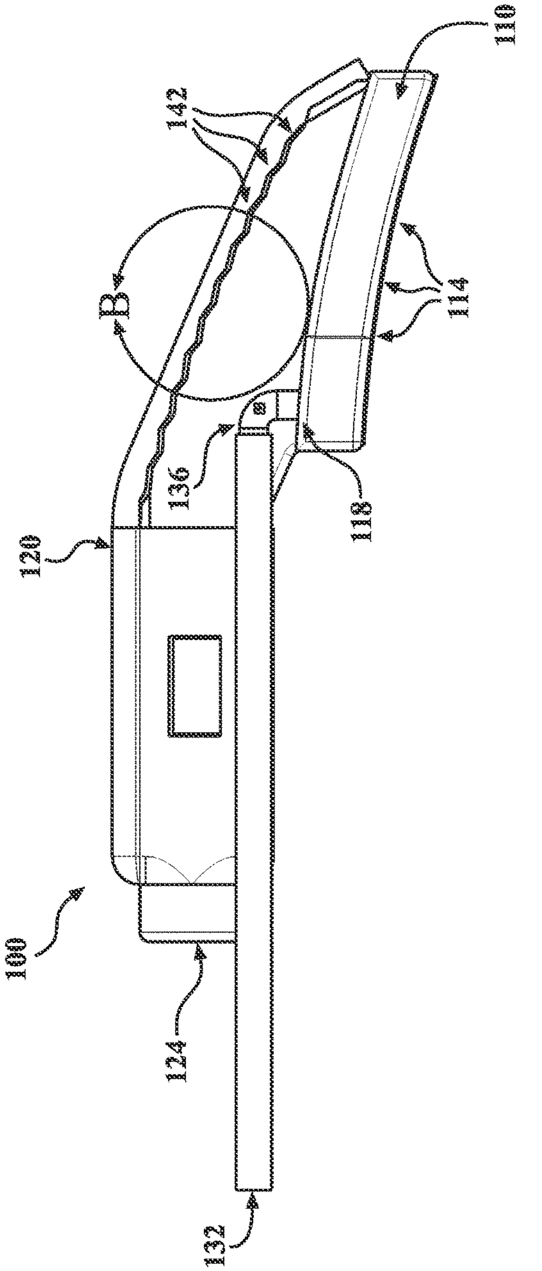
Figure 1D:
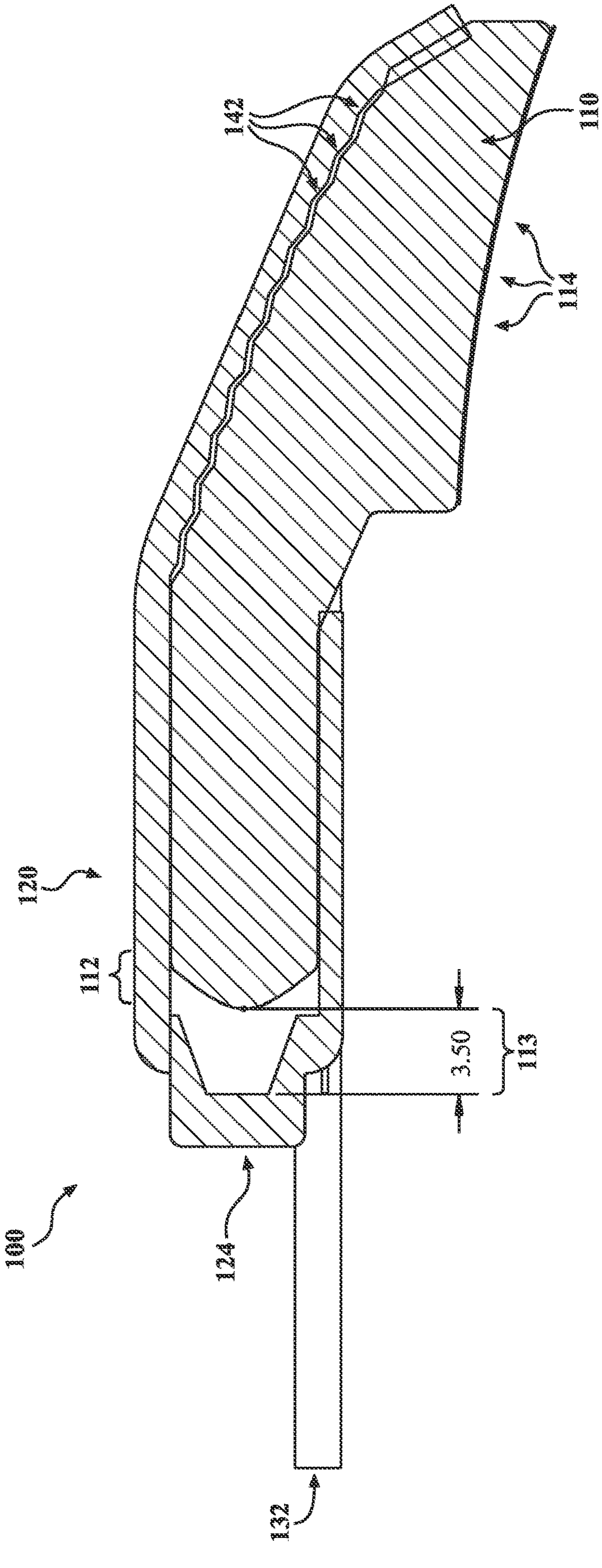
FIG. 1D is a schematic, side, cross-sectional and enlarged view of the example LDU of FIG. 1A.
Figure 1F:
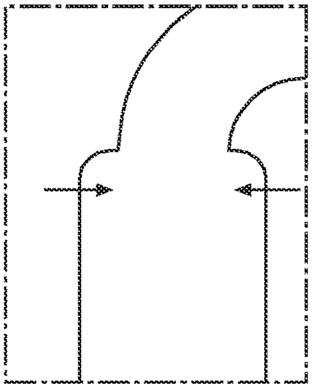
FIG. 1E is a schematic, bottom view of the example LDU of FIG. 1A.
Figure 1E:
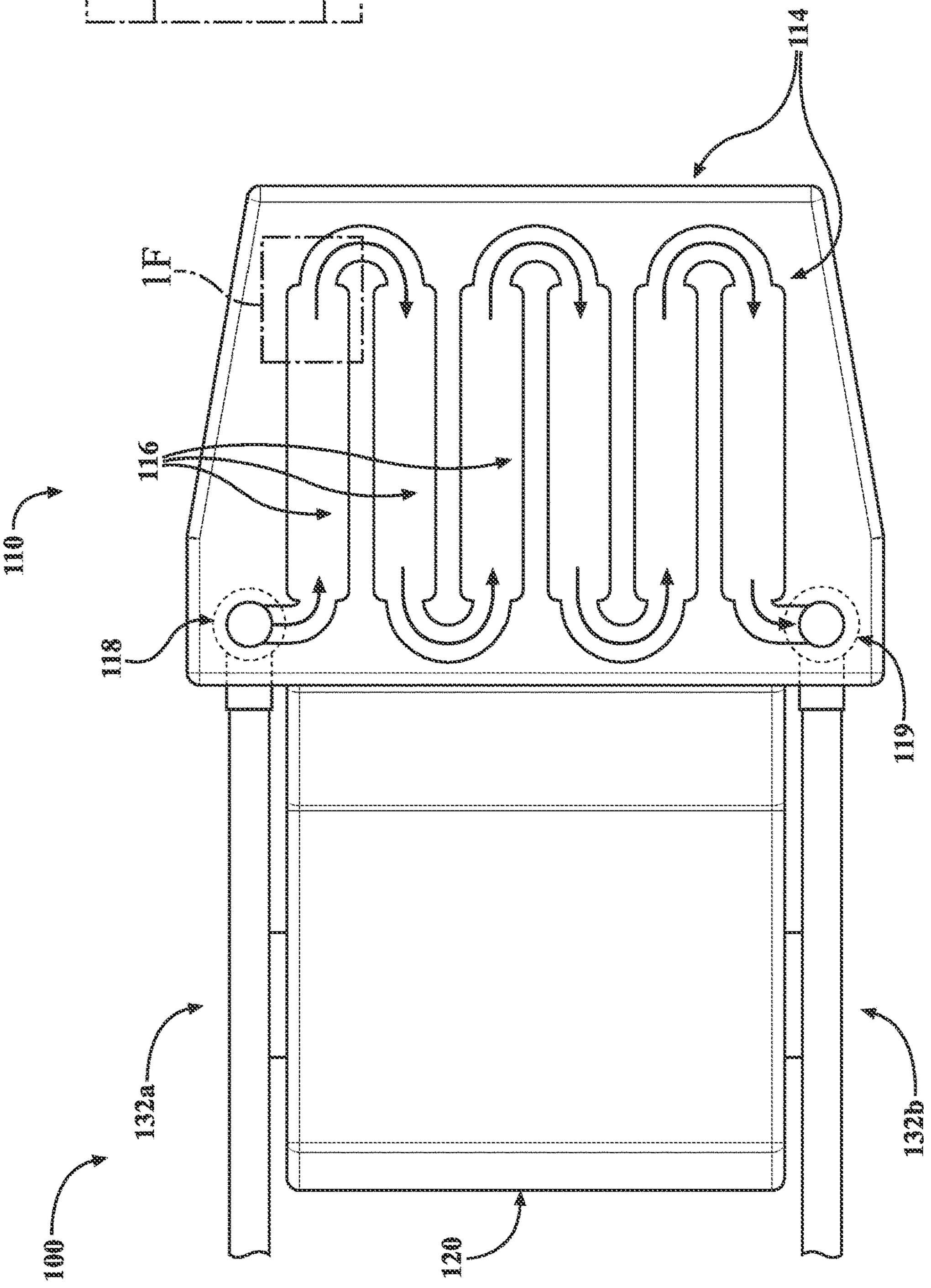
Figure 2A:
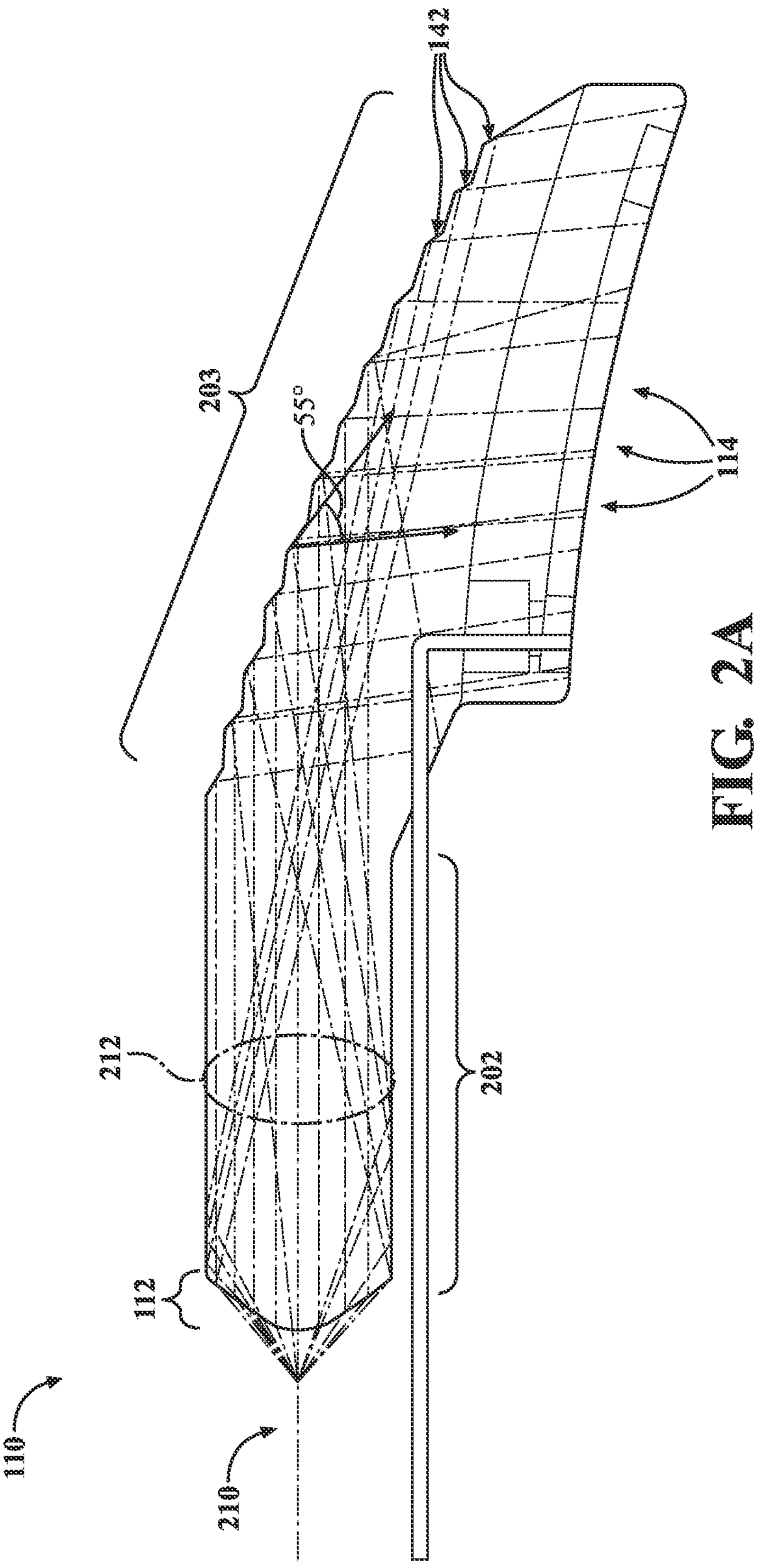
FIG. 2A is a schematic, side view illustrating example light paths through an example waveguide, according to various embodiments.
Figure 2B:
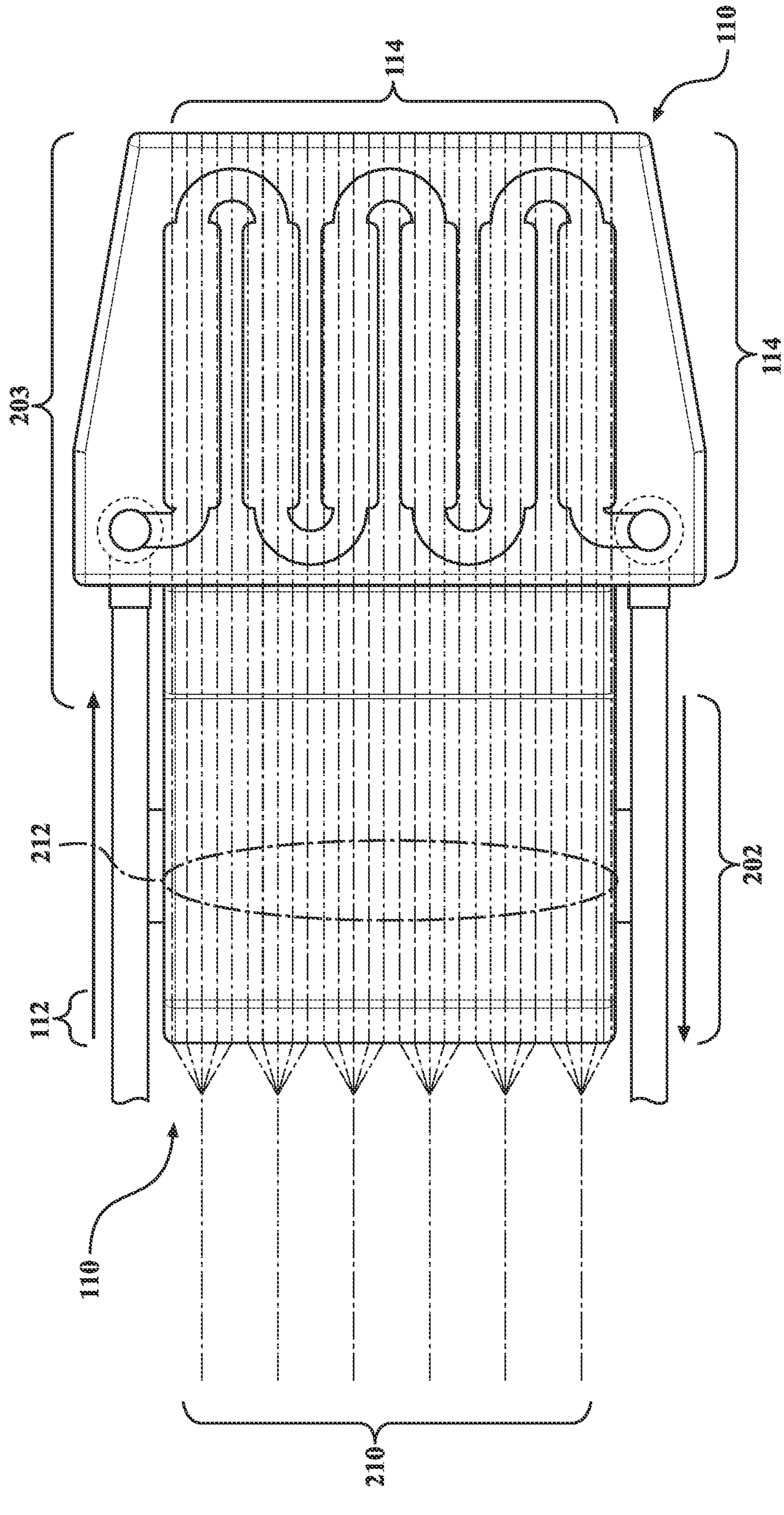
FIG. 2B is a schematic, bottom view illustrating example light paths through the example waveguide of FIG. 2A.
Figure 2C:
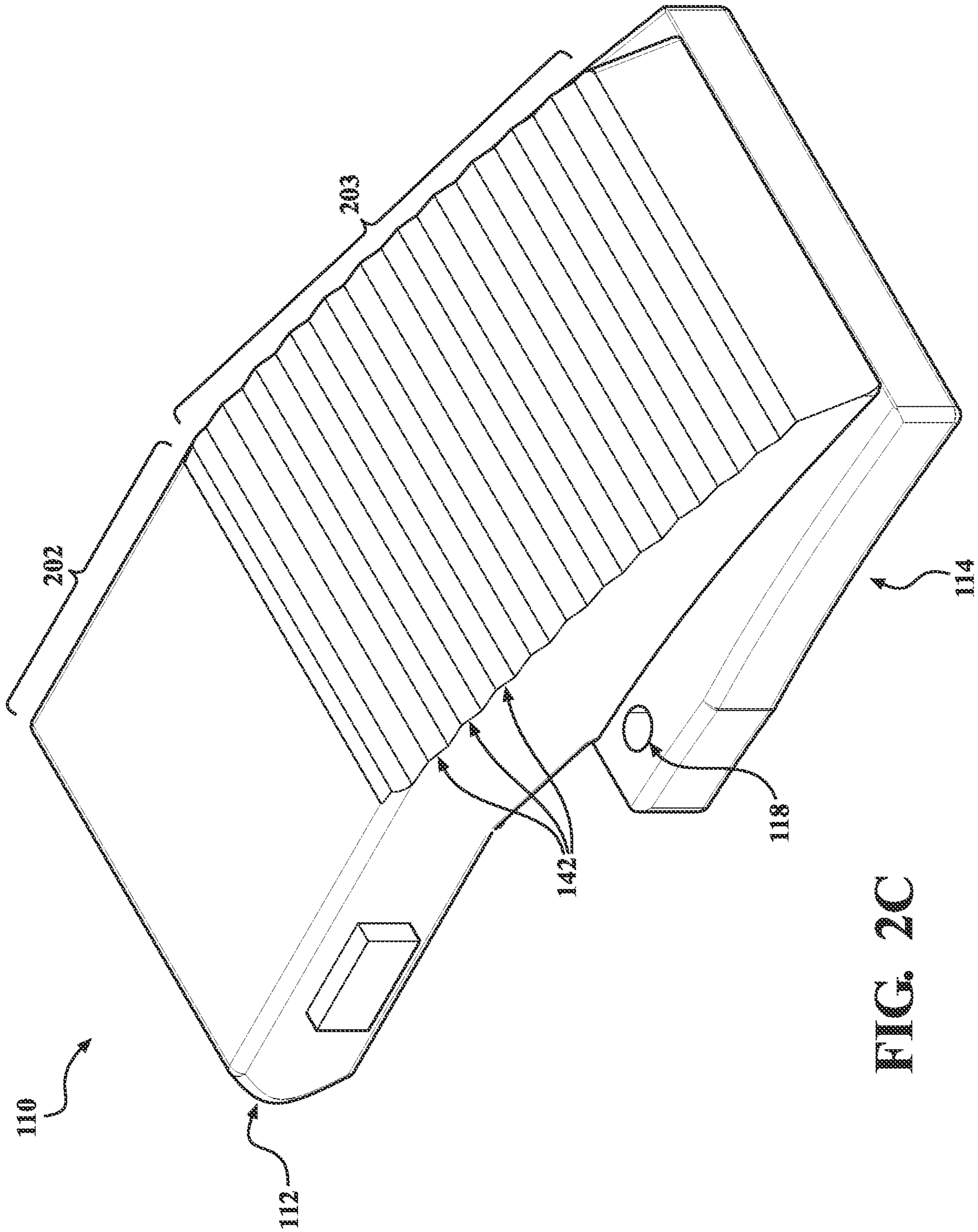
FIG. 2C is a perspective view of the waveguide of FIG. 2A.
Figure 2D:
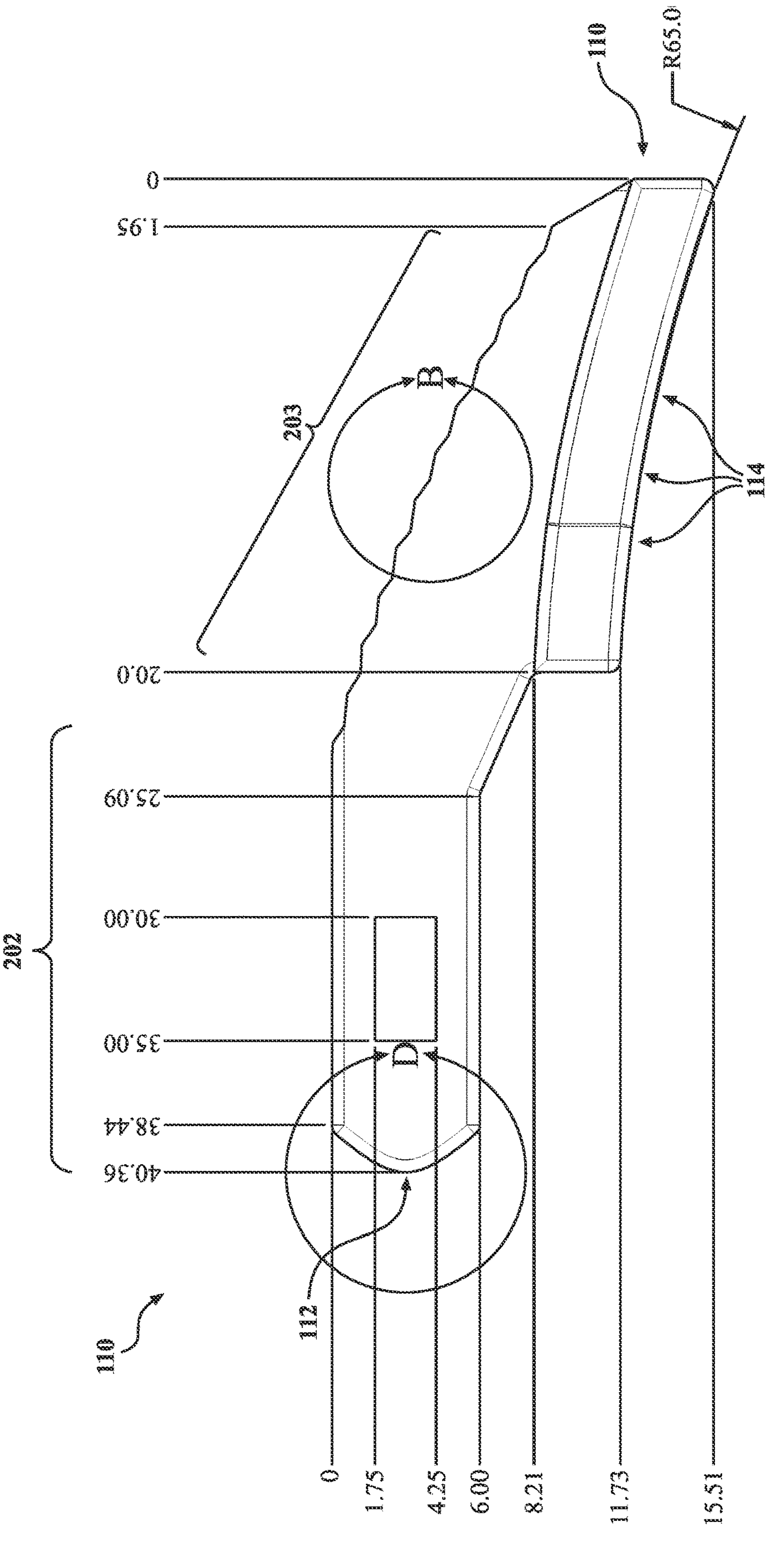
FIG. 2D is a left side view of the waveguide of FIG. 2A.
Figure 2E:
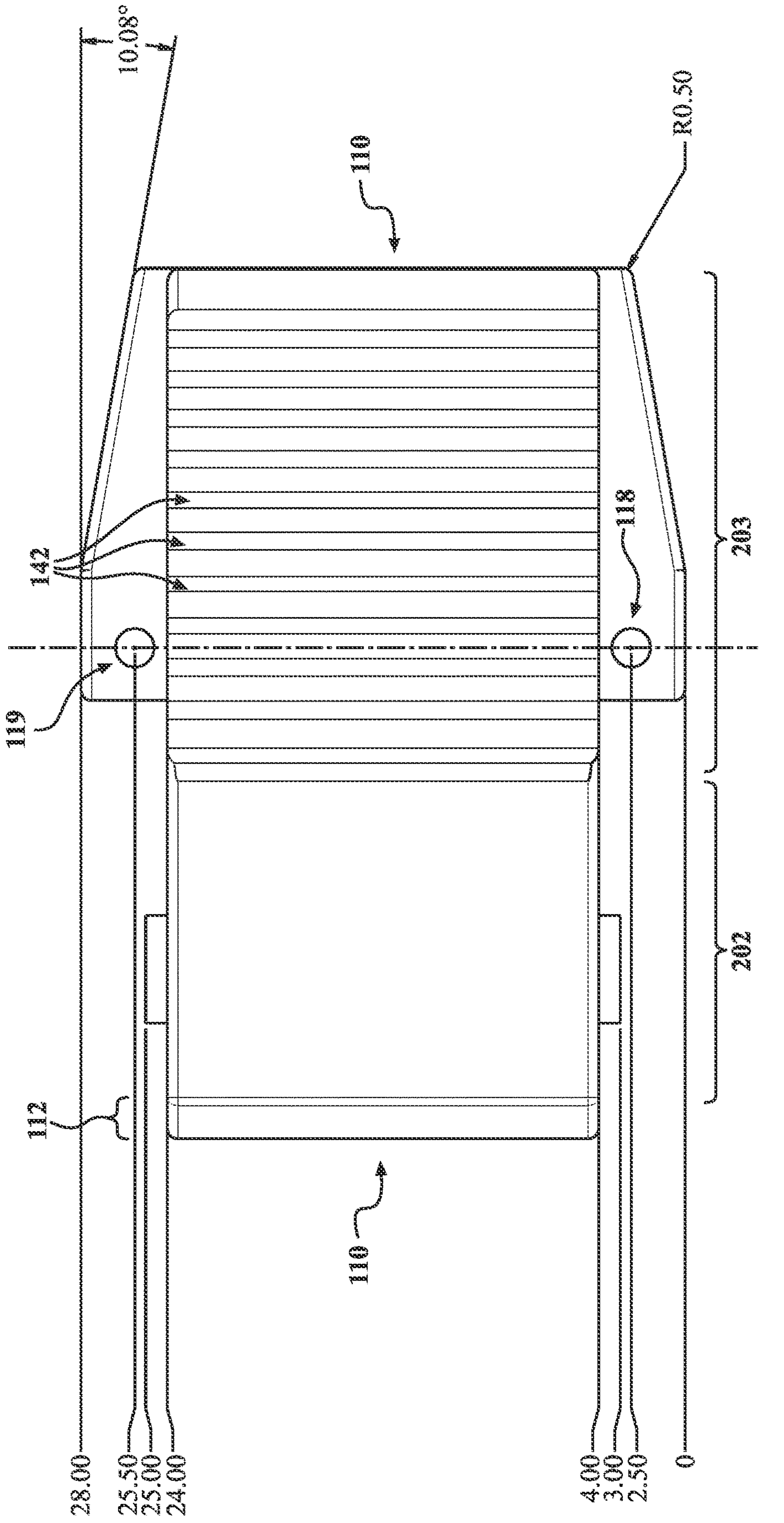
FIG. 2E is a top view of the waveguide of FIG. 2A.
Figure 2F:
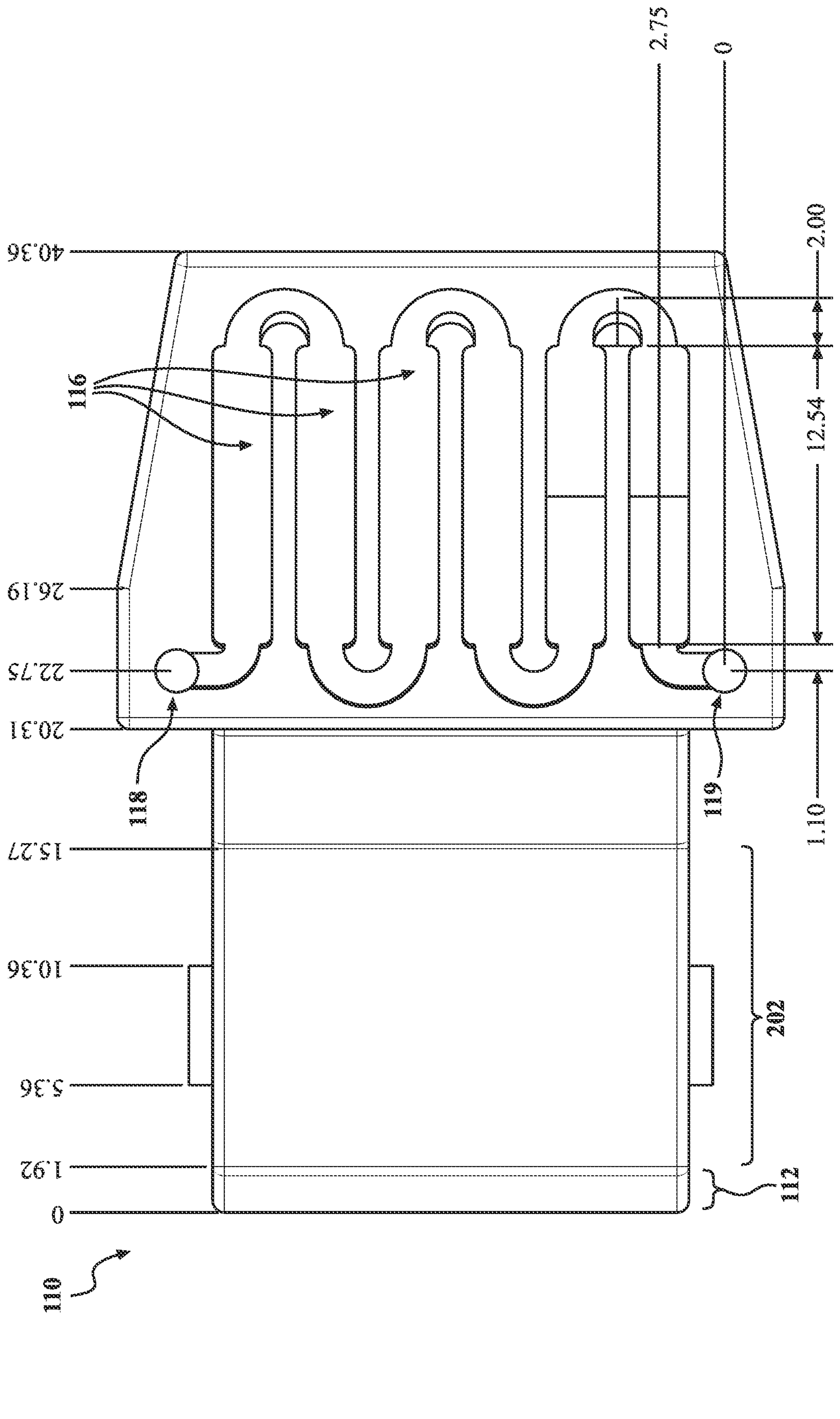
FIG. 2F is a bottom view of the waveguide of FIG. 2A.

In certain embodiments, the waveguide 110 may include one or more channels 116 (see, e.g., FIGS. 1E and 2F). The channel(s) 116 can be configured to circulate coolant (e.g., water) within the waveguide 110 as described herein. For example, the channel(s) 116 may circulate coolant within the waveguide 110 to absorb excess heat at the emitting surface 114. A first end of the channel(s) 116 may include an inlet 118 (see also, e.g., FIGS. 1B, 1C, 1E, 2C, 2E-2G). A second end of the channel(s) 116 may include an outlet 119 (see, e.g., FIGS. 1E and 2E-2G). The inlet 118 and the outlet 119 may each include a receiving mechanism (e.g., a female interface of a male to female coupling mechanism) configured to couple to a tube that connects to a coolant reservoir.

In certain embodiments, the LDU 100 may include a housing 120 formed from one or more sections. For example, the housing 120 can be comprised of two sections (e.g., that form a clam shell design). The sections may be coupled to each other via one or more fasteners (e.g., screws, hinges, brackets, clips, etc.). In another example, the housing 120 is comprised of a single section. In general, the housing 120 may be comprised of any suitable material(s) having the characteristics as described herein. For example, the housing 120 can be plastic (e.g., polyoxymethylene (POM)). In some cases, the housing 120 may be formed via injection molding or milling, but any suitable manufacturing technique may be used to form the housing 120.

In some embodiments, the housing 120 may include a cavity to house and/or otherwise retain the waveguide 110. The housing 120 may include an input/output (I/O) connector 124 configured to couple to optical signal input(s) (e.g., a fiber optic cable or other leads/tips) from an optical source (e.g., a laser or energy source). The I/O connector 124 may include one or more slots (e.g., v-groove slots) configured to receive an optical signal input. In some cases, the I/O connector 124 may include one or more electrical connection(s) to couple to an assembly as described herein. The housing 120 may retain optical signal input(s) and the waveguide 110 such that the optical signal input(s) are positioned proximate the waveguide 110. The optical signal input(s) may be positioned proximal to the waveguide 110 at a predetermined focal distance as described herein. The housing 120 may be configured to house the waveguide 110 such that the emitting surface of the waveguide 110 may be placed proximal or adjacent to a tissue surface (e.g., a skin surface) of a subject to be treated.

In certain embodiments, one or more interior walls or faces of the housing 120 may be coated and/or otherwise covered by a reflective layer. The reflective layer may include a non-metallic or metallic coating. In an example, the non-metallic coating may be polyethylene. In another example, the metallic coating may be gold, aluminum, or copper. The reflective layer may reflect light (e.g., NIR light) propagating within the waveguide 110, such that light incident to the one or more interior walls is contained within the housing 120. The NIR light propagating from an optical source may exit the waveguide 110 and reflect off an interior wall of the housing 120 via the reflective layer.

In certain embodiments, the LDU 100 may include a cooling system 130. The cooling system 130 may include one or more conduits 132 (e.g., tubes). Each of the conduit(s) 132 may be configured to carry a coolant to and/or from the channel(s) 116 of the waveguide 110. For example, a first conduit 132 may carry chilled coolant to the channel(s) 116, while a second conduit 132 may carry warmed coolant from the channel(s) 116, where the warmed coolant has absorbed thermal energy from the waveguide 110. In general, the coolant can be any suitable fluid, e.g., water. In an example, the coolant may be sterile, deionized water. In some cases, a first end of each tube 132 may include a fitting 136. A second end of each tube may be coupled to a coolant chiller as described herein. Each fitting 136 may be coupled to the waveguide 110 via an inlet 118 or an outlet 119. Each fitting 136 may comprise a barbed fitting (e.g., a male interface of a male to female coupling mechanism), such that a fitting 136 may be inserted into an inlet 118 or an outlet 119. A fitting 136 may remain coupled to the inlet 118 or the outlet 119 via the barbed fitting as described herein.

In certain embodiments, each fitting 136 may include a temperature sensor. In some cases, the temperature sensor may be waterproof. The temperature sensor may be coupled to the interior of the fitting 136, such that the temperature sensor may measure a temperature within the fitting 136. In some instances, each temperature sensor may be coupled to one or more cables 134. Each cable 134 may be configured to communicate an electrical signal (e.g., comprising temperature measurement information) to a controller or other external location. The cable(s) 134 may be electrically coupled to the I/O connector 124. In certain embodiments, for fittings 136 coupled to the inlet 118 and the outlet 119 of the channel(s) 116 of the waveguide 110, temperatures measured at the inlet 118 and the outlet 119 may be compared to determine a change in temperature for the coolant flowing through the channel(s) 116.

FIG. 1B is an assembled view of the example LDU 100. As described herein, the LDU 100 may include the waveguide 110. The waveguide 110 may be retained by the housing 120. The housing 120 may include the I/O connector 124 configured to couple the LDU 100 to optical signal input(s) of an optical source as described herein. The waveguide 110 may include the channel(s) 116 (not shown in FIG. 1B) as described herein, where each of the channels 116 is configured to circulate coolant proximal to the emitting surface 114 of the waveguide 110. The cooling system 130 may deliver and collect coolant from the channel(s) 116 via the conduits (e.g., tubes) 132. Each of the conduits 132 may couple to the LDU 100 at the waveguide 110, where a fitting 136 of each conduit 132 may facilitate coupling to a corresponding inlet 118 or outlet 119 (not shown in FIG. 1B) of the waveguide 110.

FIG. 1C is an enlarged view of the side of the example LDU 100. As shown in FIG. 1C, the LDU 100 may include the waveguide 110 retained by a housing 120. In certain embodiments, as described herein, the waveguide 110 may include an emitting surface 114. The emitting surface 114 may be concave, such that the emitting surface can conform to a surface (e.g., a skin surface of a subject) on which the LDU 100 is positioned. In other cases, the emitting surface 114 may be convex. In an example, the emitting surface 114 may have a curve radius in a range from 3 cm to 10 cm (e.g., approximately 6.5 cm), in either the concave or convex orientation. The curve radius of the emitting surface 114 may be configured to conform to a tissue surface with minimal deformation, thereby reducing an air gap between the emitting surface 114 and the surface on which the LDU 100 is positioned. In some cases, the curve radius of the emitting surface 114 may be selected based on the target user of the LDU 100 and/or a system that includes one or more LDUs 100 as described herein. In other cases, the emitting surface 114 may be flat.

In certain embodiments, as shown in the cross-sectional view in FIG. 1C, the waveguide 110 may be retained within the housing 120 such that a gap 144 exists between the extraction features 142 of the waveguide 110 and an outer face of the housing 120. Based on the waveguide 110 being flexible and/or compressible (e.g., due to being comprised of silicone) as described herein, the presence of the gap 144 may enable the waveguide 110 to conform to the surface on which the LDU 100 is placed.

FIG. 1D is an interior cross-sectional view of the side of the example LDU 100. In some cases, the waveguide 110 may include a lens 112. The lens 112 may be comprised of silicone. In an example, the lens 112 may be molded into the waveguide 110. That is, the lens feature 112 may form an NIR light input surface. Further, the lens 112 may receive and focus optical signals from one or more optical sources. The lens 112 is proximate to the at least one NIR light source, and may be configured to at least substantially collimate (see, e.g., FIG. 2A) the treatment NIR light from the at least one NIR light source and convey substantially collimated light in a first direction through the waveguide.

The optical source(s) may emit NIR light capable of treating ischemia/reperfusion or other injuries as described herein, e.g., light having a wavelength of 750 nm and/or 940 nm. The lens 112 may direct the received optical signals to one or more of the reflective extraction features 142 of the waveguide 110 as described herein. In general, the lens 112 can have any suitable shape, e.g., an aspherical shape or an acylindrical shape. The I/O connector 124 may be coupled to any suitable number of optical sources, e.g., in a range of 1-10 optical sources, 2-8 optical sources, or 4-6 optical sources. In certain embodiments, the I/O connector 124 may be coupled to a range of 1-100 optical sources. The waveguide 110 may receive and redirect optical signal(s) from each of the optical sources. In certain embodiments, the waveguide 110 and/or the I/O connector 124 may be configured to separate the lens 112 and the optical source(s) by a predetermined focal distance 113, which can be any suitable distance. In an example, as shown in FIG. 1D, the focal distance 113 between an optical source and the lens 112 may be approximately 3.5 mm+2 mm. Other focal distances 113 may be used based on the application of the LDU 100, the configuration of the waveguide 110 (e.g., the shape of the lens 112), the wavelength of the emitted optical signal(s), and/or the angle divergence of the optical signal(s).

FIG. 1E is a bottom view of the example light delivery unit (LDU) 100. As described herein, the LDU 100 may include the waveguide 110 retained by the housing 120. Each of the one or more tubes 132 may be coupled to the channel(s) 116 of the waveguide at an inlet 118 or an outlet 119 via a fitting 136. As shown in FIG. 1E, the LDU 100 may include an emitting surface 114. Optical signal(s) from the optical source(s) may be emitted by the waveguide 110 via the emitting surface 114. The optical signal(s) may propagate through (e.g., normal to) the channel(s) 116 to reach a surface (e.g., a skin surface of a user).

The emitting surface 114 may be configured to have any suitable area (e.g., in a range from 1 $cm^2$ to 200 $cm^2$, e.g., 4 $cm^2$). The area of the emitting surface 114 may be configured based on an application of the waveguide 110. The channel(s) 116 may comprise a subset of the area of the emitting surface 114. In some cases, the channel(s) 116 may comprise at least 20% of an area of the emitting surface (e.g., in a range from 50-80%). In some cases, the channel(s) 116 may be molded within the waveguide 110. In an example, as shown in FIG. 1E, the channel(s) 116 may comprise a single channel in a serpentine configuration. The walls of the channel(s) 116 may be parallel and/or non-slanted. In an example, the walls of the channel(s) 116 may be rectangular.

In certain embodiments, sections of the channel(s) 116 that are in contact with optical signals may have a greater diameter than sections of the channel(s) 116 that are not in contact with optical signals. As shown in FIG. 1E, the diameter of the channel(s) 116 may be configured to be larger in specific area(s). The diameter of the channel(s) 116 may be configured to be larger in the area(s) through which a majority (e.g., at least 50%, at least 60%, at least 70%, at least 80%, and/or at least 90%) of the optical signal propagates, such that the flow of the coolant is slowed in sections where the channel diameter is larger (e.g., the areas through which the optical signals centrally propagate). In some cases, the slowed flow of coolant in the sections where the channel diameter is larger may increase heat exchange efficiency between the coolant and the area proximal to the channel(s) 116. In some cases, one or more eddies may form in the sections where the channel diameter is larger, which may cause turbulent flow of the coolant through the channel(s) 116. Turbulent flow of the coolant within the channel(s) 116 may increase heat exchange efficiency between the coolant and the area proximal to the channel(s) 116. In some cases, the channel(s) 116 may be coated and/or otherwise sealed with a film. The film may be an optically clear film (e.g., transparent to NIR light) that is configured to increase heat exchange efficiency and facilitate propagation of the optical signal(s) through the waveguide 110. The film may include a refractive index that is equivalent or approximately equivalent to the refractive index of the waveguide 110. The film may adhere to, or be part of, the emitting surface 114 to seal (e.g., hermetically seal) the channel(s) 116. In an example embodiment, the film may be an ultra-thin silicone film.

In some embodiments, as described herein, coolant may circulate through the channel(s) 116. Coolant supplied from a tube 132*a* may enter the channel(s) 116 via an inlet 118. The inlet 118 may include a temperature sensor that measures the temperature of the coolant (e.g., chilled coolant) at the inlet 118. The coolant may circulate through the channel(s) 116. In some cases, the coolant may absorb thermal energy from the area proximal to the channel(s) 116. In an example, the coolant may absorb energy generated from emitting NIR light at a skin surface of a user. The coolant may flow through the channel(s) 116 as shown in FIG. 1E. The coolant (e.g., warmed coolant) may exit the channel(s) 116 to a tube 132*b* via an outlet 119. The coolant exiting the channel(s) 116 of the waveguide 110 may be supplied to a coolant chiller and recirculated to the LDU 100.

Configuration of a Waveguide

FIG. 2A is a side view of the example waveguide 110 illustrating example optical input and light paths through the waveguide 110. As shown, the waveguide 110 may include a lens 112. The lens 112 may focus a received optical input 210 (e.g., light energy) into one or more focused optical signals 212 (e.g., light rays). In some cases, the lens 112 can diffuse or disperse a single optical input into several optical signals 212 that travel through the waveguide 110. The waveguide can include a light entry portion 202, which can be an elongated portion of the waveguide 110 through which the optical signals 212 propagate after being focused and/or diffused/dispersed by the lens 112. In some cases, the waveguide 110 may include an extraction portion 203 comprising one or more step-like extraction features 142 onto which the optical signals 212 can be delivered from the light entry portion 202. In general, any suitable number of extraction features 142 can be used, e.g., at least three extraction features. The extraction feature(s) 142 may be molded within the waveguide 110, such that each extraction feature 142 is slanted at an angle relative to the direction perpendicular to the emitting surface 114 and/or a skin surface of a user. In various embodiments, each extraction feature 142 may be configured to be slanted at angle depending on the application for which the waveguide 110 is used. For example, a slant angle may be configured in a range from 35 degrees to 75 degrees (e.g., 55 degrees). In other words, the plurality of extractive surfaces 142 on a surface of the waveguide is configured to reflect the substantially light (e.g., collimated light) through the light emitting surface 114 to a subject. At least some of the extractive surfaces of the plurality of extractive surfaces 142 may be angled in a range of 35 to 75 degrees to a direction approximately normal to the subject. Further, the plurality of extractive surfaces may be configured to create a substantially uniform NIR light output across the light emitting surface.

In some cases, all extraction features 142 can be oriented at the same angle. In other cases, different extraction features 142 can be oriented at different angles. Each extraction feature 142 (the surfaces off which the light reflects) can be configured to redirect at least one optical signal 212 towards the emitting surface 114 of the waveguide 110, such that the at least one optical signal propagates through the emitting surface 114 approximately normal to the emitting surface 114 and/or a skin surface of a user. In some cases, the extraction feature(s) 142 may be configured to redirect optical signal(s) such that an optical signal output distribution of the waveguide 110 is substantially uniform across the emitting surface 114. For example, an output power distribution across the emitting surface 114 can be substantially uniform. In some embodiments, to determine the uniformity of the optical signal output distribution across the emitting surface 114 of the waveguide 110, the area of the emitting surface 114 may be segmented into one or more pixels. In some cases, an area of each pixel of the pixel(s) may be equivalent. In an example, the emitting surface 114 may be segmented into five pixels. During operation of the waveguide 110, a power density (e.g., $mW/cm^2$) may be measured for each pixel. A maximum power density and a minimum power density from the pixel(s) of emitting surface 114 may be determined based on the measured power densities of the pixel(s). A surface power density uniformity (SPDU) metric as described by Equation 1 may be calculated based on the maximum power density and the minimum power density. Equation 1 may be described as follows:

$$SPDU = 1 - \frac{\text{Max}_{PD} - \text{Min}_{PD}}{\text{Max}_{PD} + \text{Min}_{PD}} \times 100\% \qquad \text{Equation 1}$$

As described by Equation 1, SPDU may be based on a function of "$\text{Max}_{PD}$" and "$\text{Min}_{PD}$", where "$\text{Max}_{PD}$" may be equivalent to the maximum power density of a pixel of the pixel(s) and "$\text{Min}_{PD}$" may be equivalent to the minimum power density of a pixel of the pixel(s). In an example, for "$\text{Max}_{PD}$" equal to 100 $mW/cm^2$ and "$\text{Min}_{PD}$" equal to 20 $mW/cm^2$, the determined SPDU of the emitting surface 114 may be approximately 33% according to Equation 1. In some embodiments, the SPDU through the emitting surface 114 may be configured in a range from 10-100%. In an example, the SPDU through the emitting surface 114 may be 50%.

In some embodiments, the waveguide 110 can deliver an optical signal with an efficiency in a range of 20% to 100%, 30% to 90%, 40% to 80%, or 50% to 70%. As used herein, efficiency is calculated as a percentage of optical signal 110 that is incident upon lens 112 that exits emitting surface 114.

In some cases, as described herein, one or more faces or surfaces of the waveguide 110 may be covered and/or otherwise coupled to a reflective material. In an example, top faces, side faces, and one or more extraction features of the waveguide 110 may include the reflective material. The lens 112 and the emitting surface 114 may not be covered by a reflective material. The reflective material may help to contain one or more optical signals 212 within the waveguide 110, such that optical signals 210 enter the waveguide 110 only through the lens 112 and exit the waveguide 110 only through the emitting surface 114.

The optical input 210 may include one or more optical signal(s). In an example, the optical signal(s) may include a combination of approximately 750 nm and 940 nm light originating from one or more optical sources (e.g., a laser source or energy source). The extraction feature(s) 142 may redirect the focused optical signal(s) 212 towards the emitting surface 114. The focused optical signal(s) 212 may exit the emitting surface 114, e.g., approximately normal to the emitting surface 114 and may be used in therapeutic applications as to be described herein (e.g., treatment of IR or other injuries).

FIG. 2B is a bottom view of the example waveguide 110 illustrating an example optical input 210. As described herein, the waveguide 110 may include the lens 112, the extraction feature(s) 142, and the emitting surface 114. The waveguide 110 may receive an optical input 210. As shown in FIG. 2B, the optical input 210 may comprise multiple (e.g., in a range from 1-10 optical inputs, e.g., 6 optical signals as shown). The lens 112 may focus the optical input 210 into the focused optical signal(s) 212, which may propagate through the waveguide 110. The extraction feature(s) 142 may redirect the focused optical signal(s) 212 towards the emitting surface 114, and the focused optical signal(s) 212 may exit the emitting surface 114, e.g., approximately normal to the emitting surface 114.

Figure 2G:
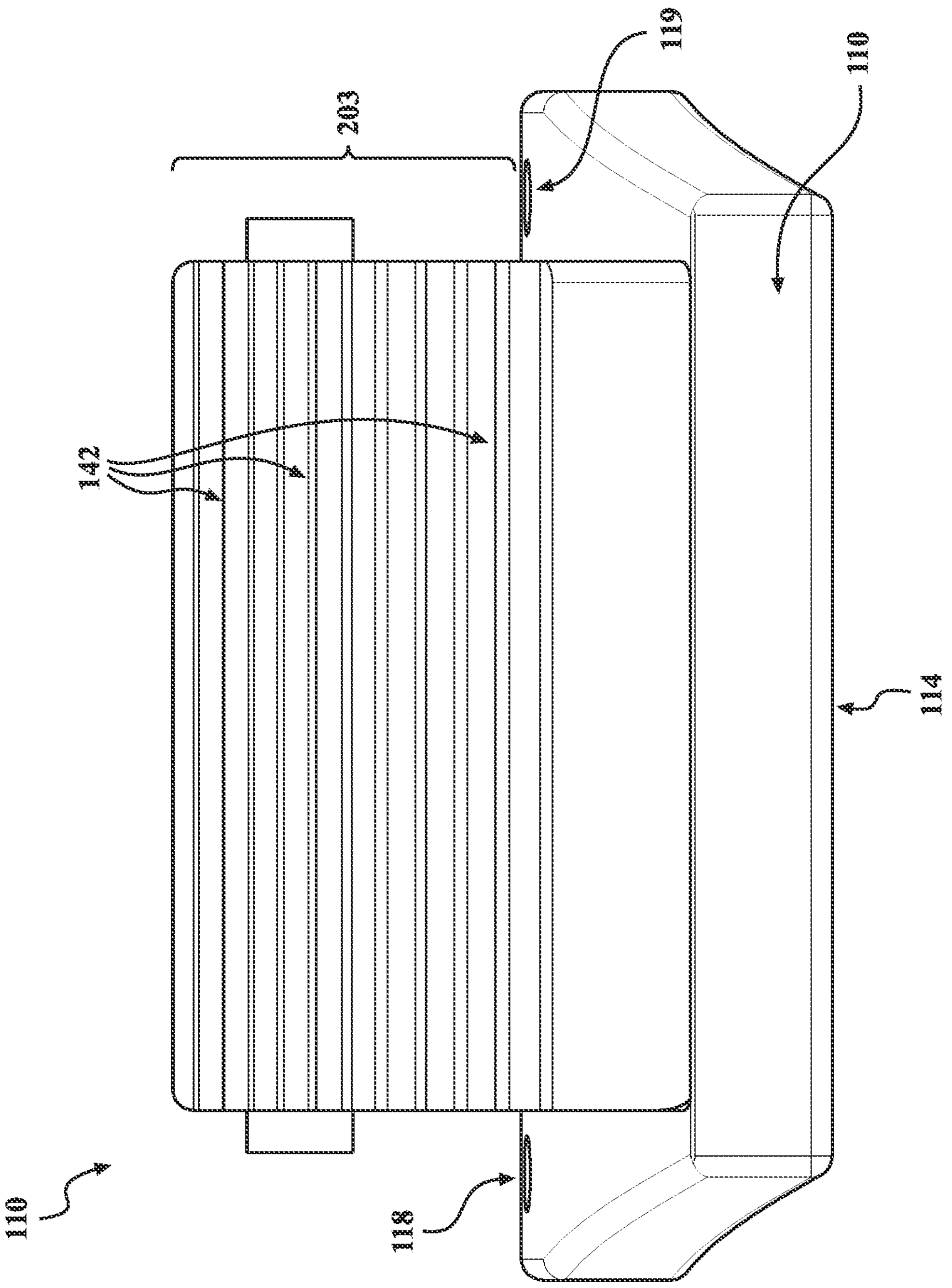
FIG. 2G is a right side view of the waveguide of FIG. 2A.
Figure 2H:
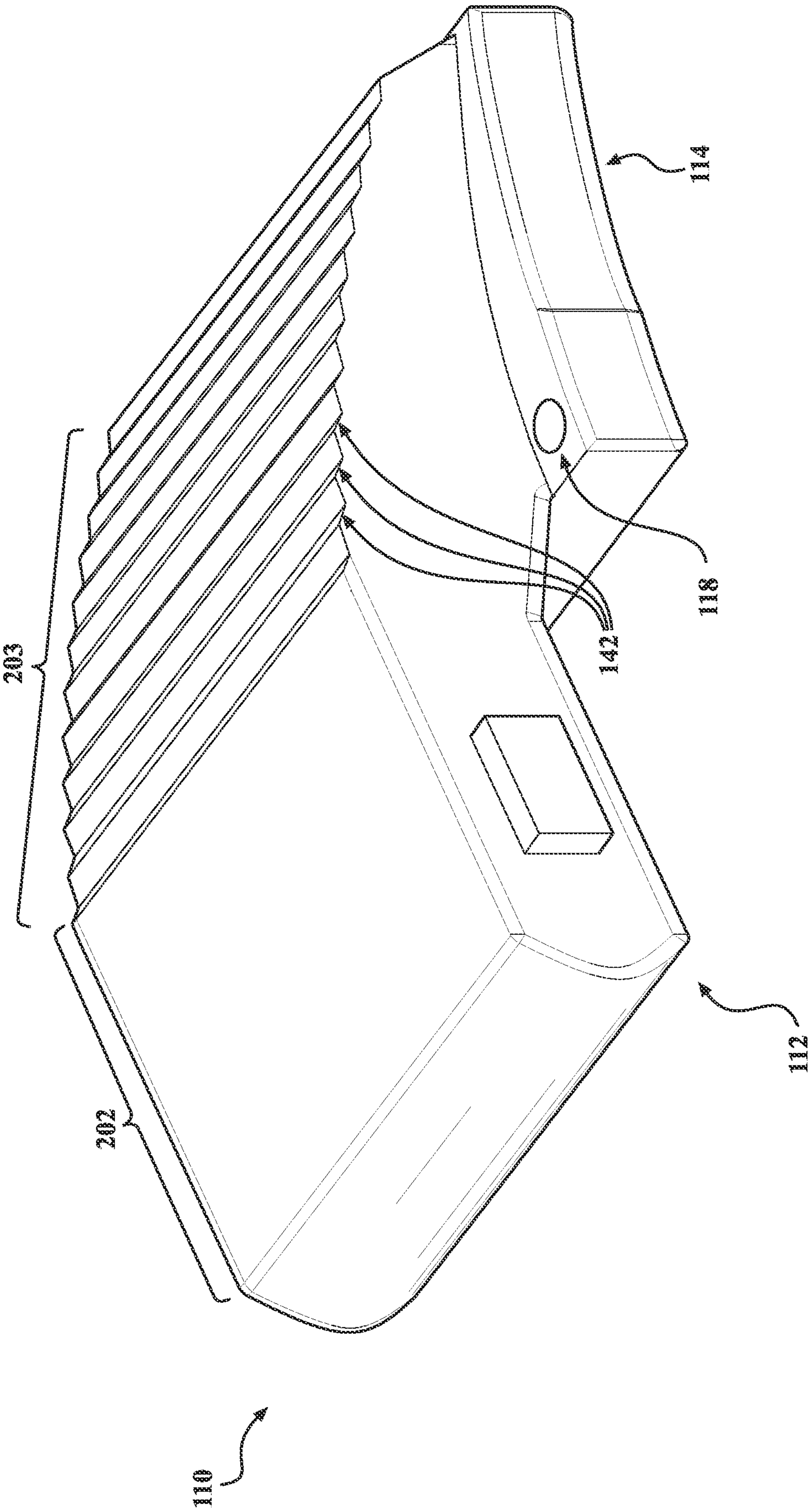
FIG. 2H is a rear view of the waveguide of FIG. 2A.

FIGS. 2C-2G are additional views of the example waveguide 110. The dimensions shown in FIGS. 2C-2G are merely examples according to certain embodiments and are not limiting of this disclosure. Any suitable dimensions may be used for the waveguide 110 without departing from the scope of the present disclosure. FIG. 2C is a perspective view of the example waveguide 110. FIG. 2D is a left side view of the example waveguide 110. FIG. 2E is a top view of the example waveguide 110. FIG. 2F is a bottom view of the example waveguide 110. FIG. 2G. is a frontal view of the example waveguide 110. FIG. 2H is a rear view of waveguide 110.

Configuration of a Therapy System

Figure 3A:
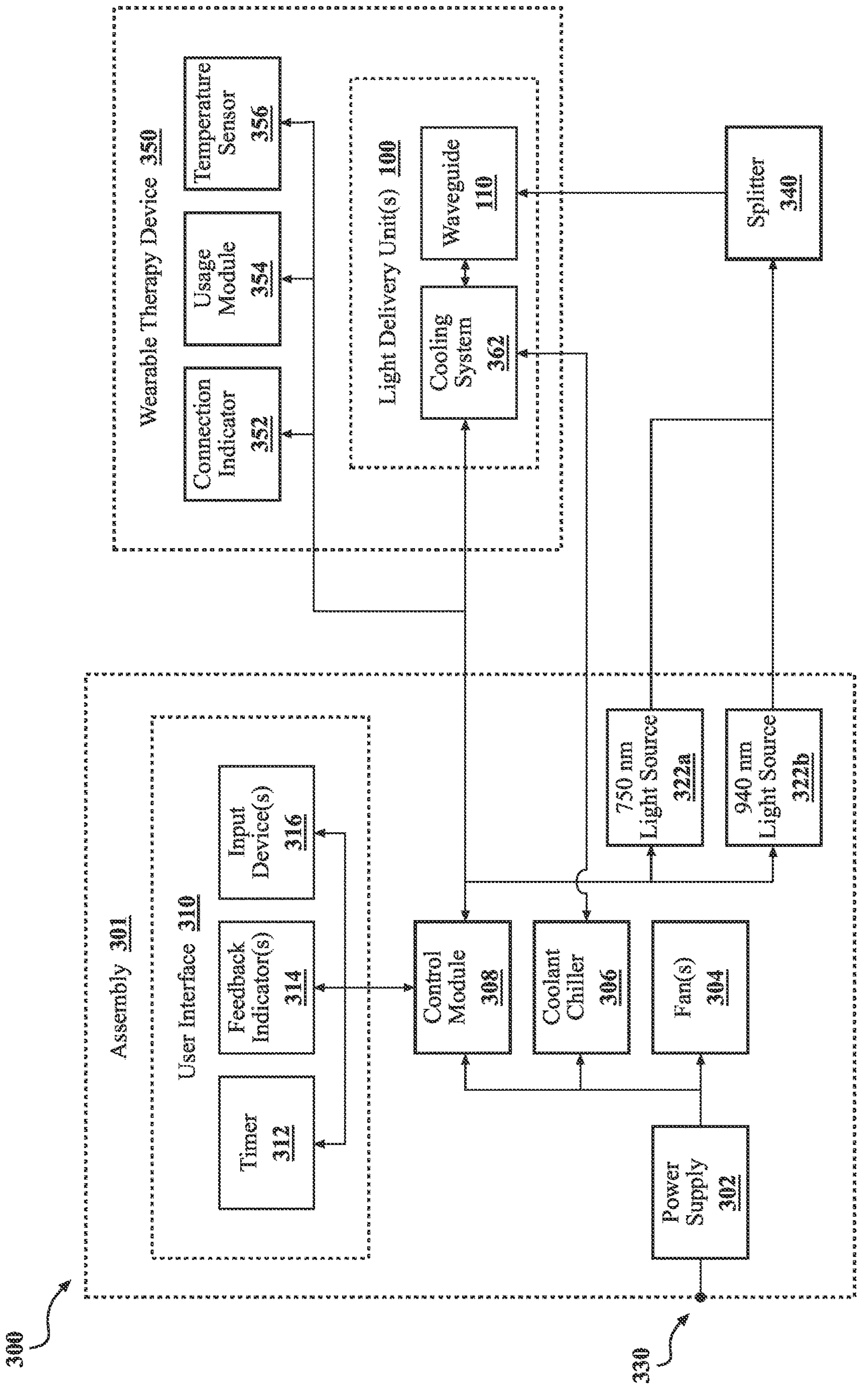
FIG. 3A is a schematic diagram of an example therapy system for NIR light therapy.

In some embodiments, one or more LDUs 100 as described herein may be included in a therapy system. In general, the therapy system can be used to treat any suitable injury. For example, the therapy system may provide therapeutic treatment to body tissue of a patient suffering the effects of ischemia/reperfusion (IR) injury via NIR light. FIG. 3A is a schematic diagram of an example therapy system 300 for providing NIR light therapy. The connections shown in FIG. 3A may include one or more of an electrical connection, an optical connection, or a fluid connection. In some cases, the therapy system 300 may include an assembly 301, a splitter 340, and a wearable therapy device 350.

In some embodiments, the assembly 301 may include a power supply 302 configured to supply power to the assembly 301. In some cases, the power supply may electrically couple to an external power source (e.g., a wall outlet) via a connection 330. In some cases, the power supply 302 may include a battery. If the power supply includes a battery, the power supply may couple to a charging station via the connection 330 to charge the battery. In some cases, the power supply 302 may be electrically coupled (e.g., to supply power) to one or more of: one or more fans 304, a coolant chiller 306, a control module 308. In some cases, the assembly 301 may include one or more fans 304. The fan(s) 304 may operate to circulate air within and/or external to the assembly 301. Based on circulating air, the fan(s) may cool the assembly 301. The fan(s) 304 may be controlled by a control module 308 as to be described herein.

In certain embodiments, the assembly 301 may include a coolant chiller 306. The coolant chiller may receive power from the power supply 302. The coolant chiller 306 may be fluidically coupled to a cooling system 362 of a wearable therapy device 350. The coolant chiller 306 may be electrically coupled to the control module 308. The coolant chiller 306 may chill coolant supplied to the coolant chiller 306. The coolant chiller may reduce or increase the temperature of received and/or stored coolant to a configured temperature. In an example embodiment, the coolant chiller 306 may chill coolant received from the cooling system 362. In some cases, the coolant chiller 306 may include a pump configured to circulate coolant. In an example, a pump of the coolant chiller 306 may circulate coolant to a cooling system 362 of a wearable therapy device 350.

In some embodiments, the assembly 301 may include a control module 308. The control module 308 may be electrically coupled to one or more of: the fan(s) 304, the coolant chiller 306, a user interface 310 (and associated components), a light source 322*a*, a light source 322*b*, and a wearable therapy device 350 (and associated components as described herein). The control module 308 may include a processor, memory, and/or a communications module (not shown in FIG. 3A). The processor may communicate with and/or otherwise control other components of the assembly 301 and/or components of the wearable therapy device 350. The memory may store one or more computer readable instructions to execute the functionality of the assembly 301 and/or the wearable therapy device 350 as to be described herein.

In some embodiments, the assembly 301 may include a user interface 310. The user interface 310 may be electrically coupled to the control module 308. The user interface 310 may include one or more display devices for displaying feedback information and/or control information for the assembly 301 and/or the wearable therapy device 350. In some cases, the user interface 310 may include a timer 312. The timer 312 may be electrically coupled to the control module 108. The timer 312 may indicate a time and/or a duration of therapy provided by the wearable therapy device 350. In an example, the timer 312 may be displayed via a liquid crystal digital (LCD) display device. Any suitable display device may be used for the timer 312. In some cases, the user interface 310 may include one or more feedback indicators 314. The feedback indicator(s) may be electrically coupled to the control module 108. The feedback indicator(s) 314 may include audible, visual, and/or haptic feedback information corresponding to the assembly 301 and/or the wearable therapy device 350. For example, a feedback indicator 314 may be a light emitting diode (LED) indicator that illuminates to indicate that the assembly 301 and the wearable therapy device 350 are on. Additionally, for example, a feedback indicator may be an audible indicator that emits a tone when therapy via the wearable therapy device 350 is completed.

In some embodiments, the user interface 310 may include one or more input devices 316. The input device(s) may be electrically coupled to the control module 308. The input device(s) 316 may be used to input information to the assembly 301 and/or the wearable therapy device 350. Information input via the input device(s) may be communicated to the control module 108. Examples of input device(s) 316 may include a touch sensitive device, a push button, a slider, a knob, and/or a microphone. The input device(s) 316 may be used to configure the assembly 301 and/or the wearable therapy device 350. In an example, an input device 316 may be used to activate the delivery of NIR light via the wearable therapy device 350. In another example, an input device 316 may be used to configure the duration for delivery of NIR light via the wearable therapy device 350.

In some embodiments, the assembly 301 may include one or more light sources 322. As shown in FIG. 3A, the assembly may include light sources 322*a* and 322*b*. In some cases, the light source(s) 322 may be laser diode assemblies. The light source 322 may be configured to emit an optical signal at approximately 750 nm (e.g., 750 nm±30 nm). The light source 322*b* may be configured to emit an optical signal at approximately 940 nm (e.g., 940 nm±30 nm). The light source(s) 322 may be configured to emit optical signals at any suitable wavelength based on the application of the assembly 301 and/or the wearable therapy device 350. As described herein, optical signals of approximately 750 nm and 940 nm may provide therapy to IR injury by modulating mitochondrial activity of body tissue under oxidative stress.

In certain embodiments, the light source(s) 322 may be optically coupled to a splitter 340. In an example embodiment, the light source 322*a* and 322*b* may be coupled to the splitter 340 via a pair of fiber optic cables. In some cases, as shown in FIG. 3A, the splitter may be external to the assembly 301 and the wearable therapy device 350. In other cases, the splitter 340 may be included in the assembly 301 or the wearable therapy device 350. The splitter 340 may be configured to splice and/or otherwise combine received optical signals into a combined optical signal. In an example, the splitter 340 may combine a 750 nm optical signal emitted by the light source 322*a* with a 940 nm optical signal emitted by the light source 322*b* to form a combined optical signal comprising both 750 nm and 940 nm light. The splitter 340 may be optically coupled to one or more LDUs 100 of the wearable therapy device 350. The splitter 340 may supply the combined optical signal to at least one LDU 100 of the wearable therapy device 350. In an example, the splitter 340 may supply the combined 750 nm and 940 nm optical signal to an LDU 100 via a fiber optic cable. The light sources 322*a* and 322*b* may emit light such that the splitter 140 delivers light at a power density in a range from 50 $\mu W/cm^2$ to 2 $W/cm^2$, e.g., approximately 1 $W/cm^2$. The light source(s) 322 of the assembly 322 may be configured to emit light at any suitable power based on the application of the assembly 301 and/or the wearable therapy device 350.

In some embodiments, the therapy system 300 may include a wearable therapy device 350. The wearable therapy device 350 may include a connection indicator 352, a usage module 354, and one or more LDUs 100. In some cases, the wearable therapy device 350 may include a support member, where the support member is configured to adhere to a body region of a patient. In general, the support member can be configured to adhere to any suitable body region, e.g., a head region, a neck region, an upper torso region, a lower torso region, an upper leg region, and/or a lower leg region. The support member may be fabricated from an elastic fabric material. In an example, the elastic fabric material may be comprised of a cotton/spandex blended fabric material or a polyester/spandex blended fabric material. In some cases, the support member may be any combination of a strap, a cap, or a helmet. In some cases, the support member may be disposable. The support member may be configured in one or more sizes. For example, the support member may be configured in small, medium, and large sizes to fit an infant, child, and adult, respectively. The support member may retain the connection indicator 352, usage module 354, and LDU(s) 100. The support member may include one or more characteristics as to be described herein with respect to FIG. 3B-3E.

In some embodiments, the connection indicator 152 may be electrically coupled to the control module 308 of the assembly 301. The connection indicator may be an audible, visual, and/or haptic indicator. In some cases, the connection indicator 152 may indicate whether the assembly 301 and the wearable therapy device 350 are connected. Based on detecting a connection of the assembly 301 and the wearable therapy device 350, the control module may display an indication of the connection via the connection indicator 152. In certain embodiments, the connection indicator 152 may be an LED indicator that is illuminated when the assembly 301 and the wearable therapy device 350 are connected.

In certain embodiments, the usage module 354 may be electrically coupled to the control module 308 of the assembly 301. A control module 308 may determine usage information stored in the usage module 354, such that the control module 308 may be configured to disable the wearable therapy device 350 based on a usage threshold. Additionally or alternatively, the usage module 354 may be configured to disable the wearable therapy device 350 based on the usage threshold. In some cases, the usage module 354 may include a fuse, where the fuse may be configured to sever and/or otherwise break based on the usage threshold. In an example, applying an increased current to the fuse may cause the fuse to sever. Based on severing the fuse, the wearable therapy device 350 may be disabled. In some cases, the usage threshold may be a threshold number of uses (e.g., one use). In other cases, the usage threshold may be a threshold amount of energy delivered to the subject to be treated. A use of the wearable therapy device 350 may be defined as a usage period exceed a threshold duration of time (e.g., in a range from 2 to 8 hours). In some cases, the usage module 354 may be configured to disable the wearable therapy device 350 based on a received input (e.g., via the input device(s) 316). In an example, the therapy system 300 may receive an emergency stop input via an input device 316. Based on the received emergency stop input, the usage module 354 may disable the wearable therapy device 350.

In some embodiments, the wearable therapy device may include a temperature sensor 356. The temperature sensor 356 may be electrically coupled to the control module 308. In some cases, the temperature sensor 356 may be external to the wearable therapy device 350. In some cases, the temperature sensor 356 may be adhered to a body region of a user (e.g., a patient). The control module 108 may measure a reference temperature ($T_R$) at a body region of the user via the temperature sensor 356. $T_R$ may indicate a body temperature of a user at a position different from the position of the temperature sensors of the LDU(s) 100.

In some embodiments, the wearable therapy device 350 may include one or more LDUs 100. In various embodiments, the wearable therapy device 350 may include in a range from 1-20 LDUs, in a range from 2-18 LDUs, in a range from 3-16 LDUs, in a range from 4-14 LDUs, in a range from 5-12 LDUs, in a range from 6-10 LDUs (e.g., 6 LDUs or 8 LDUs). Each LDU 100 may include a cooling system 362, a waveguide 110, and a housing (not shown). The cooling system 362 may include one or more characteristics of the cooling system 130 as described herein with respect to FIGS. 1A-1E. In some cases, the cooling system 362 may be fluidically coupled to the coolant chiller 306 via one or more tubes. The cooling system 362 may be fluidically coupled to the waveguide 110 via the tube(s). The coolant chiller 306 may be coupled to the channel(s) of the waveguide 110 via the conduit(s) of the cooling system 362. Each of the conduits of the cooling system 362 may be configured to carry coolant to or from the channel(s) of the waveguide 110. In an example, a first conduit may carry chilled coolant from the coolant chiller 306 to an inlet of the channel(s) of the waveguide 110, while a second conduit may carry warmed coolant from an outlet of the channel(s) to the coolant chiller 306.

In certain embodiments, the cooling system 362 may include one or more temperature sensors. As described herein, a fitting of each tube of the cooling system 362 may include a temperature sensor, where the fitting may couple the tube to an inlet or an outlet of the waveguide 110. Each temperature sensor of the cooling system 362 may be electrically coupled to the control module 308 via a cable. A temperature sensor may be coupled to each fitting, such that the temperature sensor may measure a temperature at an area proximal to the fitting. The control module 308 may measure temperatures (e.g., coolant temperatures) at the wearable therapy device 350 via the temperature sensor(s) included in the cooling system 362. In some cases, a temperature sensor may be positioned at an inlet (e.g., inlet 118), where the temperature sensor may determine the temperature to be $T_1$. $T_1$ may be representative of a temperature of coolant entering the channel(s). In some cases, a temperature sensor may be positioned at an outlet (e.g., outlet 119), where the temperature sensor may determine the temperature to be $T_2$. $T_2$ may be representative of a temperature of coolant exiting the channel(s). The control module 308 may determine the temperature difference ($\Delta T = T_2 - T_1$) between the outlet and the inlet. AT may be used to determine the absorption of heat at a skin region of a subject to which the wearable therapy device 350 is applied. $T_R$ and $\Delta T$ may be compared (e.g., by the control module 108) to determine whether the wearable therapy device 350 is operating under expected conditions and/or to adjust the treatment parameters if necessary. In an example, a comparison of $T_R$ and $\Delta T$ may be used to determine the wearable therapy device 350 is overheating at an area on which it is positioned. In certain embodiments, a treatment regime can include different operating parameters at different stages of the treatment, which can be informed by measurements from the temperature sensors and/or implemented by the control module 308.

In certain embodiments, as described herein, an LDU 100 may include a waveguide 110. The channel(s) of the waveguide 110 may be fluidically coupled to the coolant chiller 306 via the cooling system 362 as described herein. The waveguide 110 may be optically coupled to the splitter 340. In an example embodiment, the waveguide 110 may be coupled to the splitter 340 via a fiber optic cable. The waveguide 110 may receive an optical input from the splitter 340. In an example embodiment, the optical input may be a combined optical signal comprising both 750 nm and 940 nm light. In another example embodiment, the optical input may be separate optical signals, where a first optical signal comprises 750 nm light and a second optical signal comprises 940 nm light. In some cases, if the optical input include separate optical signals, the separate optical signals may be combined into a combined optical signal comprising both 750 nm and 940 nm light. The combined optical signal may propagate incident to a lens of the waveguide 110. The lens may focus the combined optical signal into one or more focused optical signals. The focused optical signal(s) may propagate incident to one or more extraction features of the waveguide 110. The extraction feature(s) may redirect the focused optical signal(s) such that the focused optical signal(s) are approximately normal to an emitting surface of the waveguide 110. The focused optical signal(s) may propagate through the channel(s) and the emitting surface as one or more emitted optical signals. In some cases, if the wearable therapy device is worn by a subject (e.g., a patient) the emitted optical signal(s) may be incident to a tissue surface (e.g., skin surface) of the subject. The emitted optical signal(s) may propagate through the body tissue of the subject. In some cases, propagation of the emitted optical signal(s) through body tissue may provide therapy via modulation of mitochondrial activity if the body tissue is under oxidative stress.

In some embodiments, as described herein, the LDU 100 may include a housing 120. In some cases, the housing may include one or more fasteners (e.g., brackets, screws, clips, etc.) to physically couple the LDU 100 to the wearable therapy device 350.

Figure 3B:
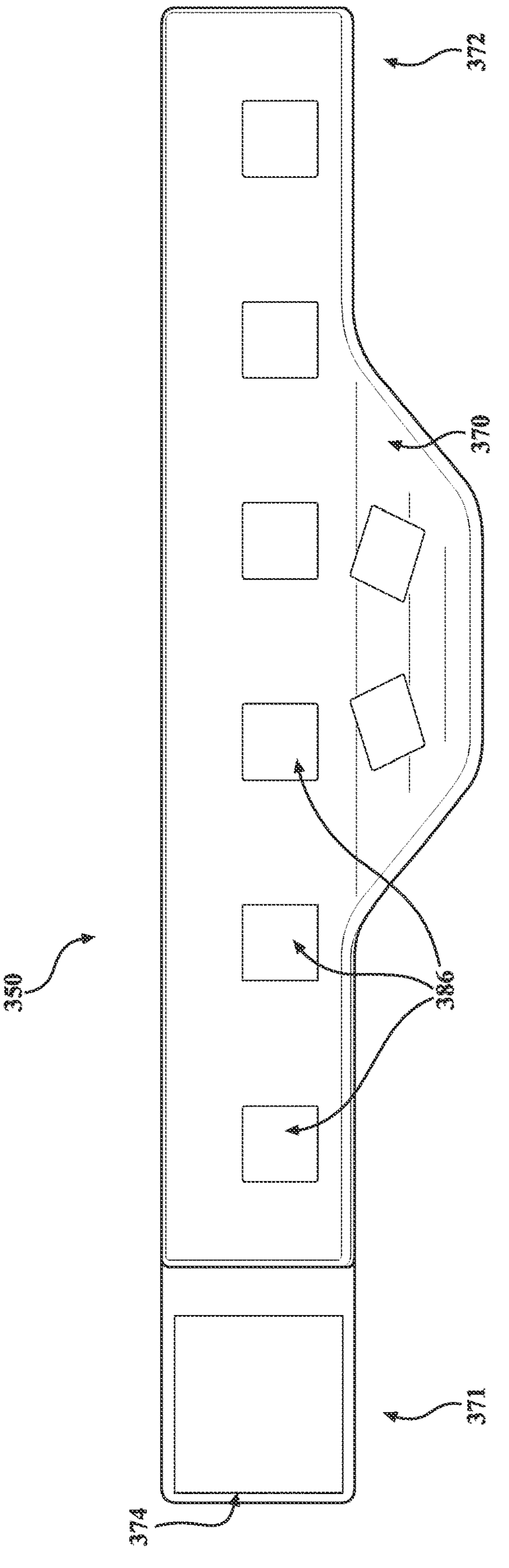
FIG. 3B is a schematic, interior view of an example wearable device of an example therapy system for providing near infrared NIR light therapy.
Figure 3C:
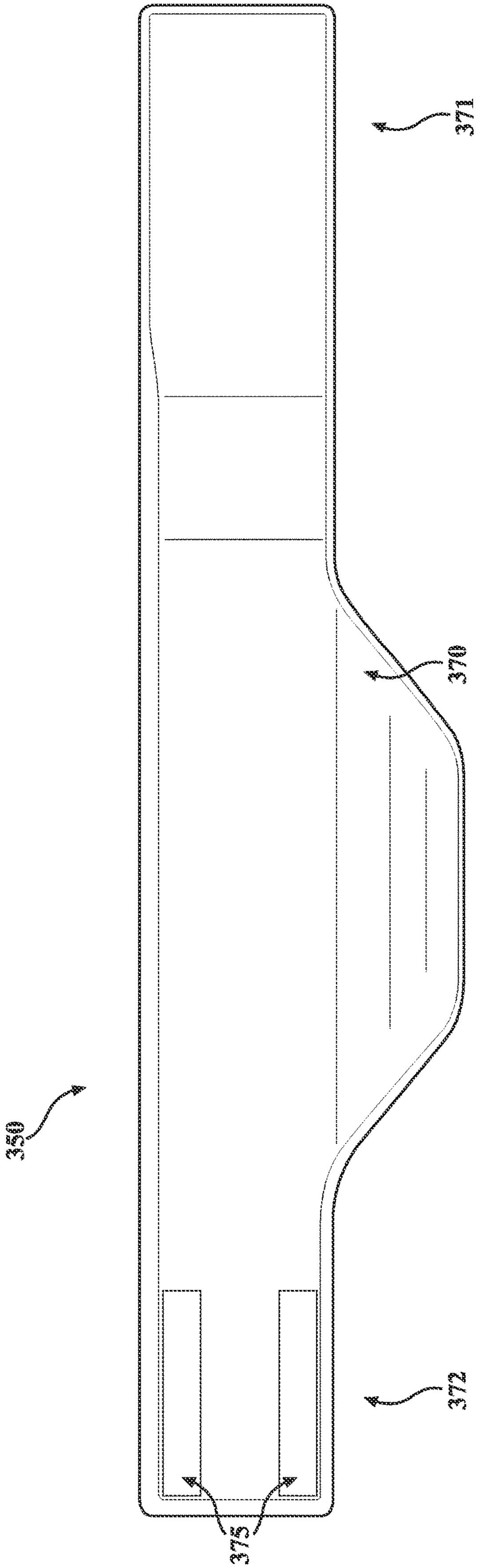
FIG. 3C is a schematic, exterior view of the example wearable device of FIG. 3B.
Figure 3D:
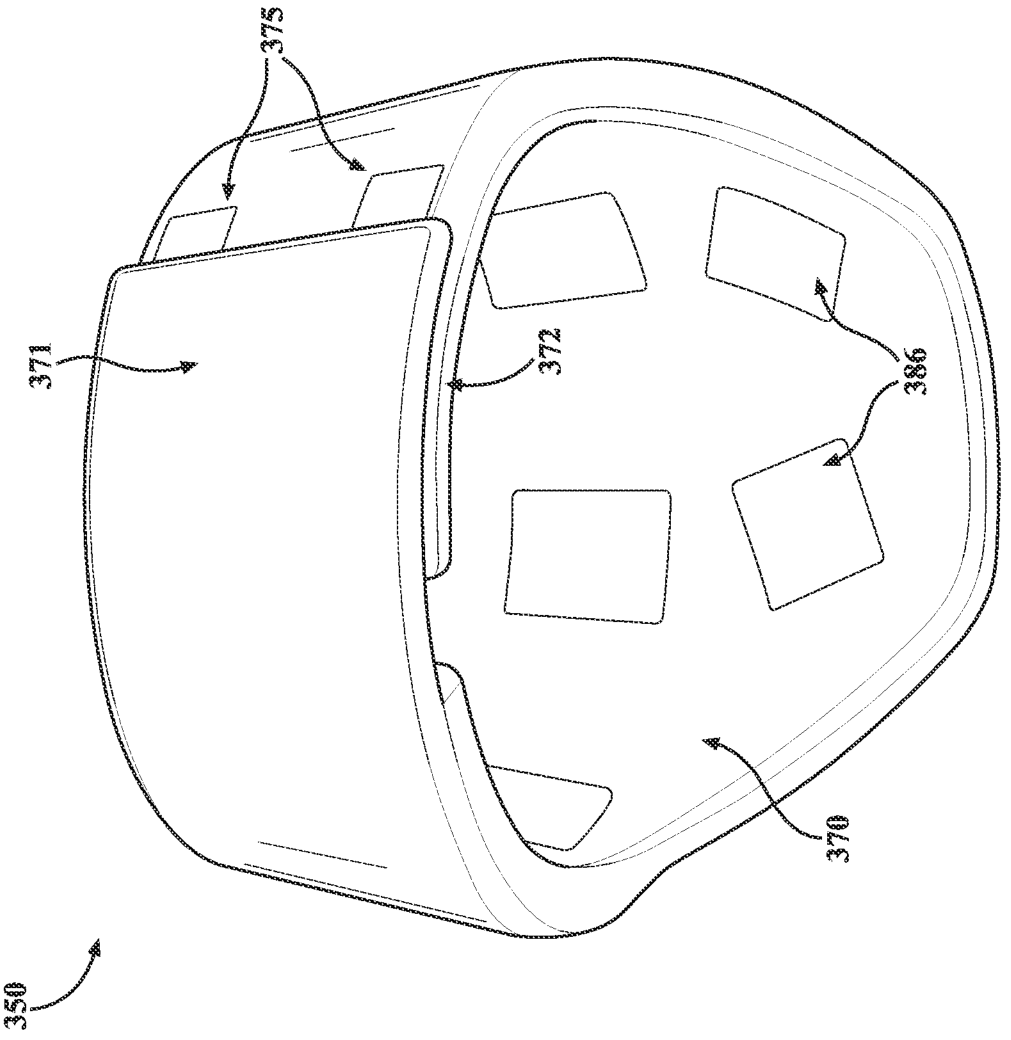
FIG. 3D is a schematic, side view of the example wearable device of FIG. 3B.

FIG. 3B is an interior view of the example wearable therapy device 350 of the example therapy system 300 for providing NIR light therapy. In some cases, as described herein, the wearable therapy device 350 may include a support member 370 configured to adhere to a body region (e.g., head region) of a patient. As shown in FIG. 3B, the support member 370 may include a first end 371 and a second end 372. The first end 371 of the support member 370 may include a strap 374. The strap 374 may removably couple to a strap 375 (not shown in FIG. 3B) to removably couple the second end 372 to the first end 371. The support member 370 may be comprised of an elastic fabric material. In an example embodiment, as shown in FIG. 3B, the wearable therapy device 350 can lie flat. In other embodiments, as shown in FIG. 3D, the wearable therapy device 350 can be wrapped. In some cases, the support member 370 may be any combination of a strap, a cap, or a helmet. In some cases, the support member 370 may be disposable. The support member 370 may be configured in one or more sizes. For example, the support member 370 may be configured in small, medium, and large sizes to fit an infant, child, and adult, respectively. The support member 370 may retain the LDU(s) 100 (not shown in FIG. 3B) to an exterior of the wearable therapy device 350 as shown in FIG. 3C. In an example, the wearable therapy device 350 may include eight LDUs 100 retained by the support member 370. In some embodiments, the wearable therapy device 350 may include one or more pads 386. The pad(s) 386 may be configured to relieve and/or otherwise prevent areas of pressure (e.g., pressure points) at a body region to which the wearable therapy device 350 is adhered. Each pad 386 may correspond to an LDU 100 of the wearable therapy device 350, where each pad 386 is positioned at an area proximal to an LDU 100 at the interior of the wearable therapy device 350. The pad(s) 386 may be comprised of a soft, gel material. In an example, the pad(s) 386 may be in a range from 2 cm-8 cm by in a range from 2 cm-8 cm (e.g., 6 cm by 6 cm).

FIG. 3C is an exterior view of the example wearable therapy device 350 of the example therapy system 300 for providing NIR light therapy. In some cases, as described herein, the wearable therapy device 350 may include a support member 370 configured to adhere to a body region (e.g., head region) of a patient. As shown in FIG. 3C, the support member 370 may include a first end 371 and a second end 372. The second end 372 of the support member 370 may include a strap 375. The strap 375 may removably couple to the strap 374 (as shown in FIG. 3B) to removably couple the second end 372 to the first end 371. In an example embodiment, as shown in FIG. 3C, the wearable therapy device 350 can lie flat. The support member 370 may retain the LDU(s) 100 (not shown in FIG. 3C) to the exterior of the wearable therapy device 350. In an example, the wearable therapy device 350 may include eight LDUs 100 retained by the support member 370.

FIG. 3D is a side view of the example wearable therapy device 350 of the example therapy system 300 for providing NIR light therapy. As shown in FIG. 3D, wearable therapy device 350 may be configured in a wrapped position. A first end 371 of the support member 370 may be coupled to a second end 372 of the support member 370 via a strap 374 (not shown in FIG. 3D) and the strap 375. Any suitable fastener may be used in place of or in addition to the strap 374 and the strap 375. The wearable therapy device 350 may be configured in a wrapped positioned to adhere to a head region of user of the therapy system 300.

Figure 3E:
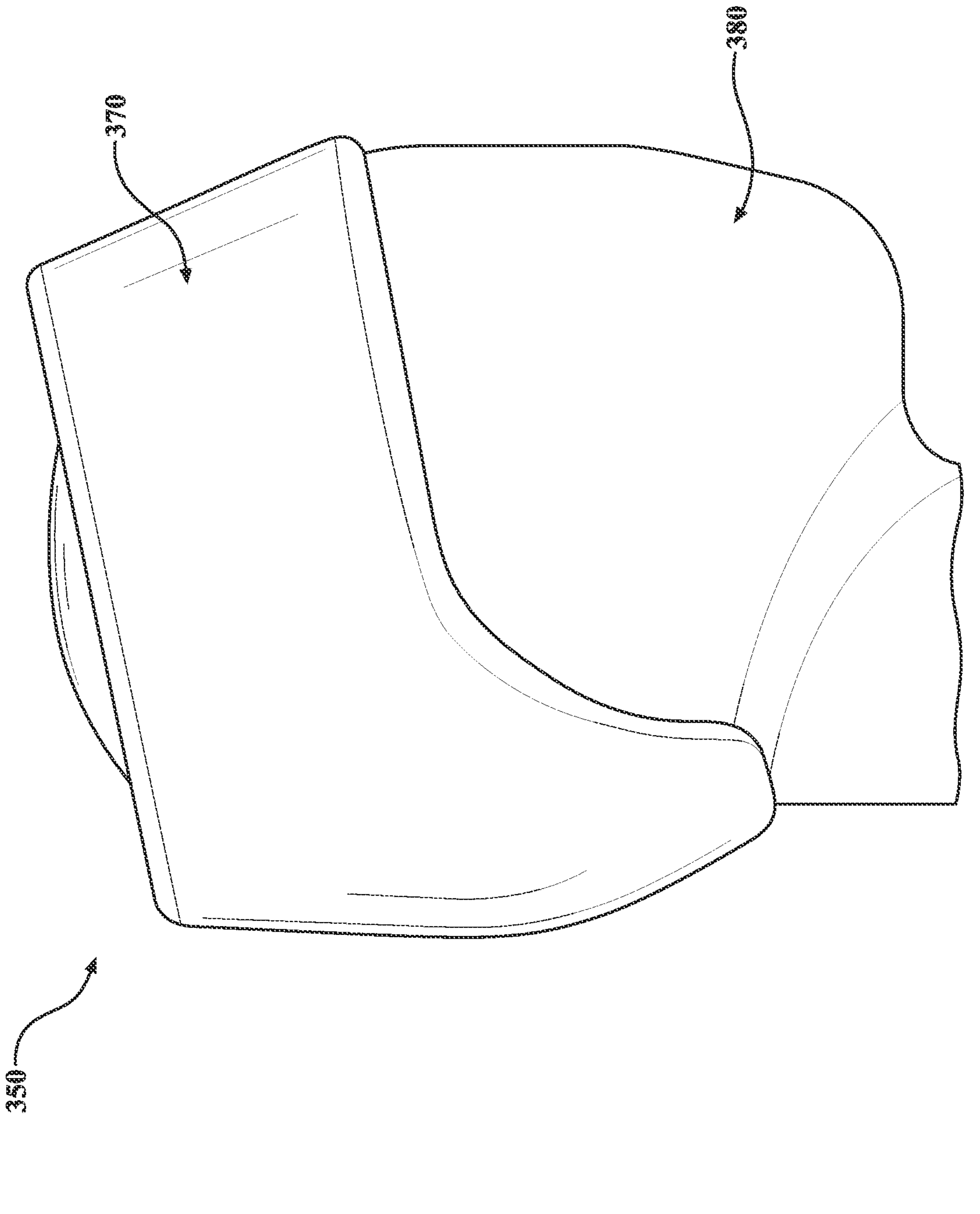
FIG. 3E is a schematic, perspective view of the example wearable device of FIG. 3B in a wrapped orientation about the head of a subject to be treated.

FIG. 3E illustrates the example wearable therapy device 350 of the example therapy system 300 as worn on the head of a user. In some cases, the wearable therapy device may be conformed to a user 380 via the support member 370. In an example embodiment, as shown in FIG. 3E, the wearable therapy device 350 may be conformed to a head region of the user 380. The wearable therapy device 350 may conform to the head region of the user 380 via the strap 374 and the strap 375 (not shown in FIG. 3E). The wearable therapy device 350 can be configured so as to strategically position the LDUs 100 (not shown in FIG. 3E) to deliver NIR light therapy to desirable tissue regions and also to avoid delivering NIR light therapy to undesirable anatomical structures (e.g., venous sinus, certain blood vessels, organs, etc.). The number of LDUs 100 and/or a position of each of the LDU(s) 100 on the support member 370 may be selected based on the particular therapeutic application and/or the characteristics of a subject (head size, venous sinus placement, etc.) of the wearable therapy device 350. In some cases, the user characteristics can be determined using medical imaging such as an X-ray, MRI, or CT scan. In an example embodiment, the wearable therapy device 350 may include eight LDUs 100, where four LDUs 100 are positioned on each hemisphere of a head region of the user 380. Such positioning can also avoid contact with certain anatomical structures. In another example, the wearable therapy device 350 may include six LDUs 100, where three LDUs 100 are positioned on each hemisphere of a head region of the user 380. Each of the LDUs 100 may conform a skin surface of the user 380. In some cases, each of the LDUs 100 may be positioned such that optical signals emitted by each LDU 100 (e.g., via a waveguide 110) are emitted approximately normal to the skin surface of the user 380.

Configuration of a Coolant I/O Mechanism

Figure 4A:
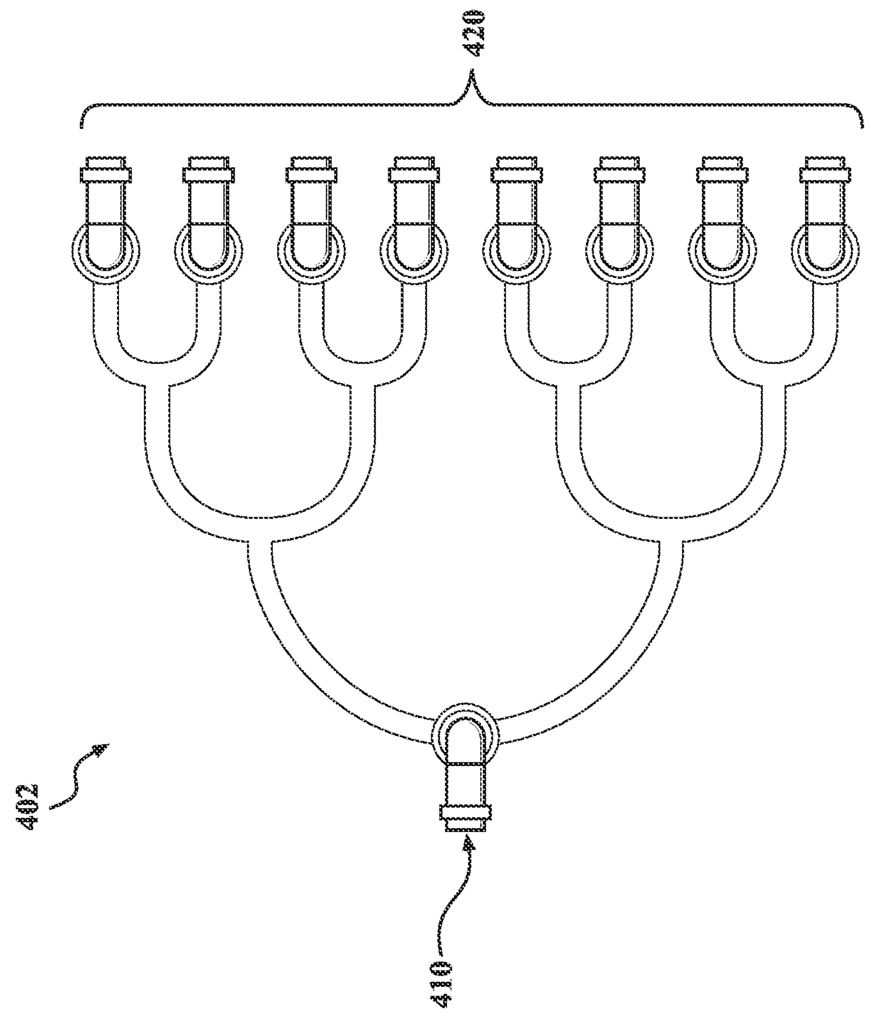
FIG. 4A is a schematic diagram of an example combiner for circulating coolant in a therapy system for providing NIR light therapy, according to various embodiments.

FIG. 4A illustrates an exemplary combiner 402 for circulating coolant in a therapy system (e.g., the therapy system 300) for providing NIR light therapy. In some cases, a tube of a cooling system of an LDU may be coupled to a combiner 402 as described herein. The combiner 402 may be comprised of one or more conduits (e.g., tubes) and one or more fittings to combine or distribute fluid from one or more sources. In an example embodiment, the combiner 402 distributes coolant from a chiller device to one or more LDUs of a wearable therapy device. In another example, the combiner may combine coolant from one or more LDUs to deliver the combined coolant to a chiller device. The combiner 402 may include a first inlet/outlet (I/O port) 410 and one or more second I/O ports 420. In some cases, fluid (e.g., coolant) may flow into the first I/O port 410 and may be distributed to the second I/O port(s) 420. In other cases, fluid (e.g., coolant) may flow into the second I/O port(s) 420 and may be combined in the first I/O port 410. In an example, as shown in FIG. 4A, the combiner 402 may include eight I/O ports 420. The combiner 402 may include any suitable number of second I/O ports 420 based on the number of LDUs included in a wearable therapy device and/or the number of combiners included in a therapy system as described herein.

Figure 4B:
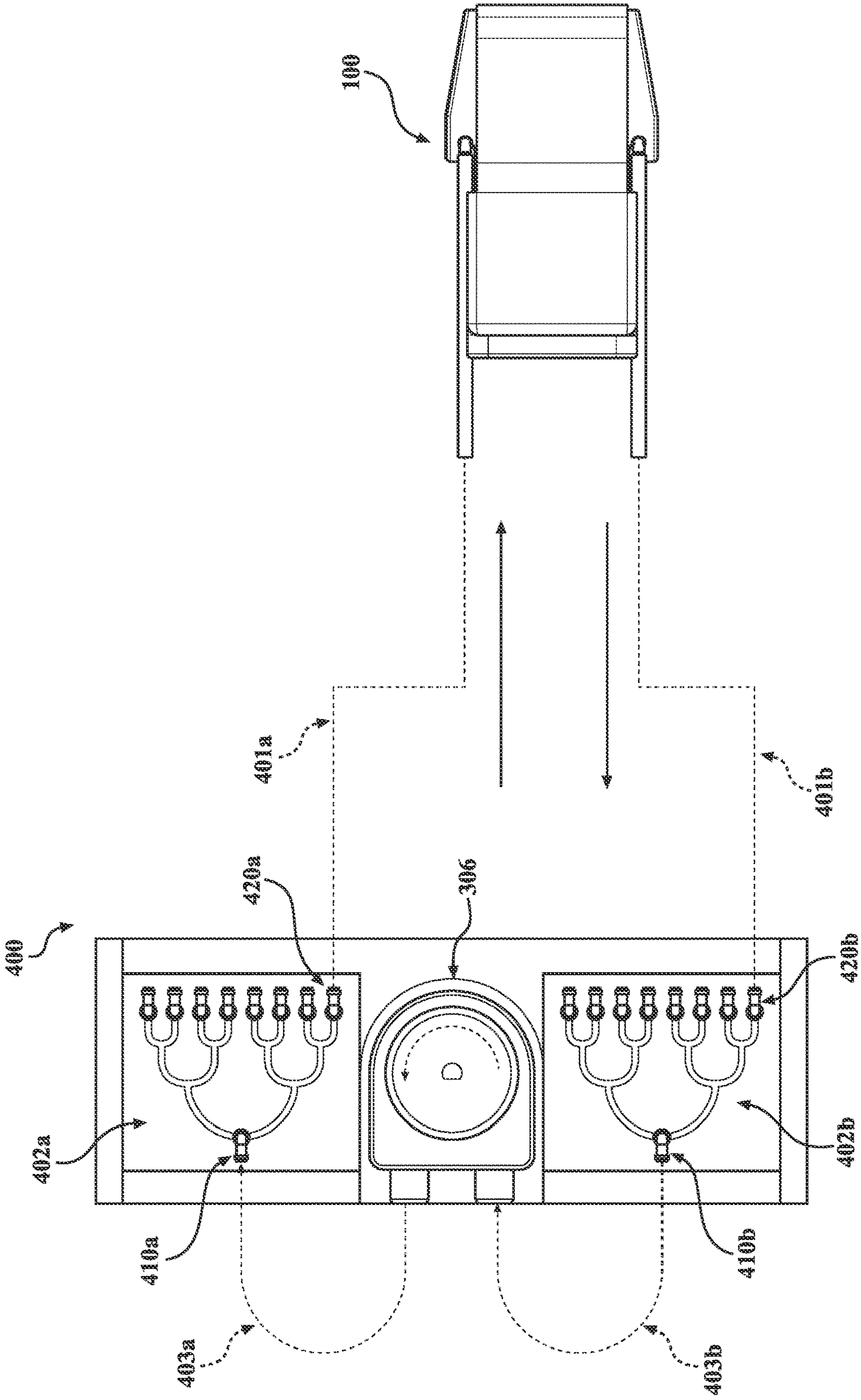
FIG. 4B is a schematic diagram of an example coolant circulation system within a therapy system for providing NIR light therapy, according to various embodiment.

FIG. 4B illustrates an example of coolant circulation via example combiners 402 within a therapy system (e.g., the therapy system 300) for providing near infrared (NIR) light therapy. For illustration purposes, the example of coolant circulation shown in FIG. 4B is shown for a single LDU 100. However, any suitable number of LDUs 100 may circulate coolant as described herein. In some cases, therapy system 400 may include one or more tubes 403. The tube(s) 403 may couple one or more combiners 402 to a coolant chiller as described herein. As shown in FIG. 4B, a therapy system 400 may include tubes 403*a* and 403*b*. In some cases, the therapy system 400 may include one or more combiners 402, where each combiner 402 is configured to combine or distribute coolant. As shown in FIG. 4B, the therapy system 400 may include combiners 402*a* and 402*b*. In some cases, the therapy system 400 may include one or more LDUs 100 as a part of a wearable therapy device as described herein. The LDU 100 may include a cooling system, where the cooling system includes one or more tubes 401 coupled to an inlet or an outlet of the LDU 100. As shown in FIG. 4B, the therapy system 400 may include tubes 401*a* and 401*b* as a part of a cooling system of the LDU 100.

In some cases, the combiner(s) 402 may be included in a wearable therapy device that comprises the LDU(s) 100. For example, a wearable therapy device may include the combiners 402*a* and 402*b*, such that tubes 401 connected to inlets and outlets of LDUs 100 may be coupled to the combiner 402*a* or the combiner 402*b* on the wearable therapy device. In other cases, the combiners 402 may be included in an assembly (e.g., the assembly 301). For example, an assembly 301 may include the combiners 402*a* and 402*b* to fluidically couple the coolant chiller 306 to the LDU(s) 100. In some cases, the combiners 402 may be included with a splitter (e.g., the splitter 340), such that the combiners 402 are external to an assembly and a wearable therapy device as described herein.

In some embodiments, the tube 403*a* may be coupled to a coolant chiller 306, such that the tube 403*a* circulates chilled coolant to a first I/O port 410*a* of the combiner 402*a*. The combiner 402*a* may receive the coolant and distribute the receive coolant to one or more second I/O port(s) 420. The tube 401*a* may be coupled to a second I/O port 420*a* of the combiner 402*a*. The tube 401*a* may receive the chilled coolant from the second I/O port 420*a* of the combiner 402*a*. The tube 401*a* may circulate the chilled coolant to an inlet of the channel(s) 116 (not shown in FIG. 4B) of the LDU 100. The chilled coolant may exit the LDU 100 as warmed coolant at an outlet of the channel(s) 116. The tube 401*b* may be coupled to the outlet of the channel(s) 116. The tube 401*b* may receive the warmed coolant from the outlet. The tube 401*b* may be coupled to a second I/O port 420*b* of the combiner 402*b*, such that the tube 401*b* circulates the warmed coolant to the second I/O port 420*b* of the combiner 402*b*. In some cases, warmed coolant originating from one or more LDUs 100 may be supplied to the second I/O ports 420 of the combiner 402*b*. The combiner 402*b* may receive the warmed coolant from the LDU 100 (and one or more other LDUs 100). The warmed coolant may converge within the combiner 402*b* at a first I/O port 410*b* of the combiner 402*b*. The tube 403*b* may be coupled to the first I/O port 410*b* of the combiner 402*b*. The tube 403*b* may receive the warmed coolant from the first I/O port 410*b* of the combiner 402*b* and may supply the warmed coolant to the coolant chiller 306 as described herein. Accordingly, coolant may be circulated between an LDU 100 and a coolant chiller 306 via the combiners 402*a* and 402*b*, such that the LDU 100 (e.g., an emitting surface of the LDU 100) may be chilled by chilled coolant and the warmed coolant originating from the LDU 100 may be chilled by the coolant chiller 306.

Configuration of an Optical and Electrical I/O Mechanism

Figure 5:
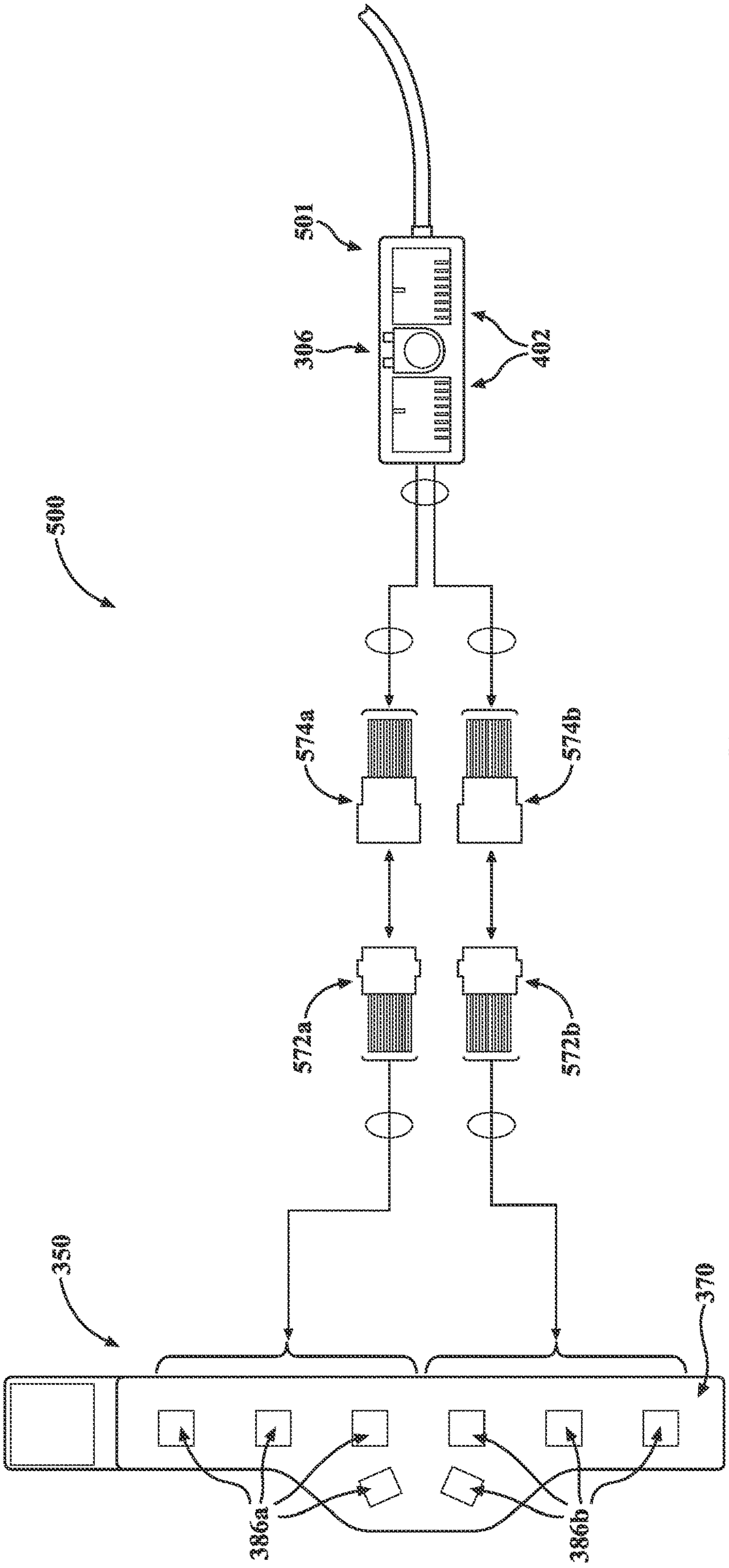
FIG. 5 is a schematic diagram of an example coupling mechanism in a therapy system for providing NIR light therapy, according to various embodiments.

FIG. 5 illustrates an example coupling mechanism in a therapy system 500 for providing NIR light therapy. In some cases, a wearable therapy device 350 may be coupled to an assembly 501 as described herein. The wearable therapy device 350 may include one or more LDUs 100 (not shown in FIG. 5), where each LDU 100 may include an I/O connector 124 as described herein. The wearable therapy device 350 may include a support member 370 configured to retain the LDU(s) 100 and adhere to a body region (e.g., head region) of a user as described herein. In some cases, the wearable therapy device 350 may include one or more connectors 572. First end(s) of a connector 572 may be coupled to one or more I/O connector(s) 124 corresponding to the LDU(s) 100. The positions of the pads(s) 386 on the interior of the wearable therapy device 350 as shown in FIG. 5 may indicate the positions of the LDU(s) 100 on the exterior of the wearable therapy device 350. In an example, as shown in FIG. 5, first ends of a connector 572*a* may be coupled to four LDUs 100 (with positioning indicated by pads 386*a*) and first ends of a connector 572*b* may be coupled to four LDUs 100 (with positioning indicated by pads 386*b*). In various embodiments, first ends of a connector 572 may be coupled to any suitable number of LDUs 100. In some embodiments, a splitter (not shown) or an assembly 501 may include one or more connectors 574. A second end of a connector 572 may be coupled to a first end of a connector 574. In an example, as shown in FIG. 5, a second end of the connector 572*a* may be coupled to a first end of a connecter 574*a* and a second end of the connector 572*b* may be coupled to a first end of a connector 574*b*. In some cases, the connector(s) 572 may be removably coupled to the connector(s) 574. In an example, the connectors 572*a* and 572*b* may be removably coupled to the connectors 574*a* and 574*b* such that the wearable therapy device 350 and the assembly 501 may be disconnected.

In some embodiments, a connector 572 may be configured as an inserting connector (e.g., a male connector of a male-female coupling mechanism). In some cases, a connector 574 may be configured as a receiving connector (e.g., a female connector of a male-female coupling mechanism. In some instances, a connector 572 and a connector 574 may physically couple based on a male-female coupling mechanism. Both a connector 572 and a connector 574 may include one or more optical channels (e.g., fiber optic cables) and electrical wires and/or cables, where the connectors 572 and 574 may optically and electrically couple to transport one or more signals. The coupled optical channels may transport an emitted optical signal (e.g., combined 750 nm and 940 nm light) from the assembly 501 to each of the LDUs 100 of the wearable therapy device 550. The coupled electrical wires and/or cables may communicate information between temperature sensors included in the wearable therapy device 350 and the assembly. In an example embodiment, a control module (e.g., the control module 308) of the assembly may determine temperature information at an inlet and outlet of each of the LDUs 560 via the coupled connectors 572 and 574.

In some embodiments, as described herein, the assembly 501 may include the coolant chiller 306. The coolant chiller 306 may be configured to chill coolant and circulate the coolant to the LDU(s) of a coupled wearable therapy device 350. In an example, as shown in FIG. 5, the assembly may include the coolant chiller 306 and a pair of combiners 402. A first combiner 402 of the pair of combiners 402 may combine coolant received from the LDU(s) 100 for chilling by the coolant chiller 306. A second combiner 402 of the pair of combiners 402 may distribute coolant chilled by the coolant chiller 306 to the LDU(s) 100.

Further Description of Certain Embodiments

Figure 6:
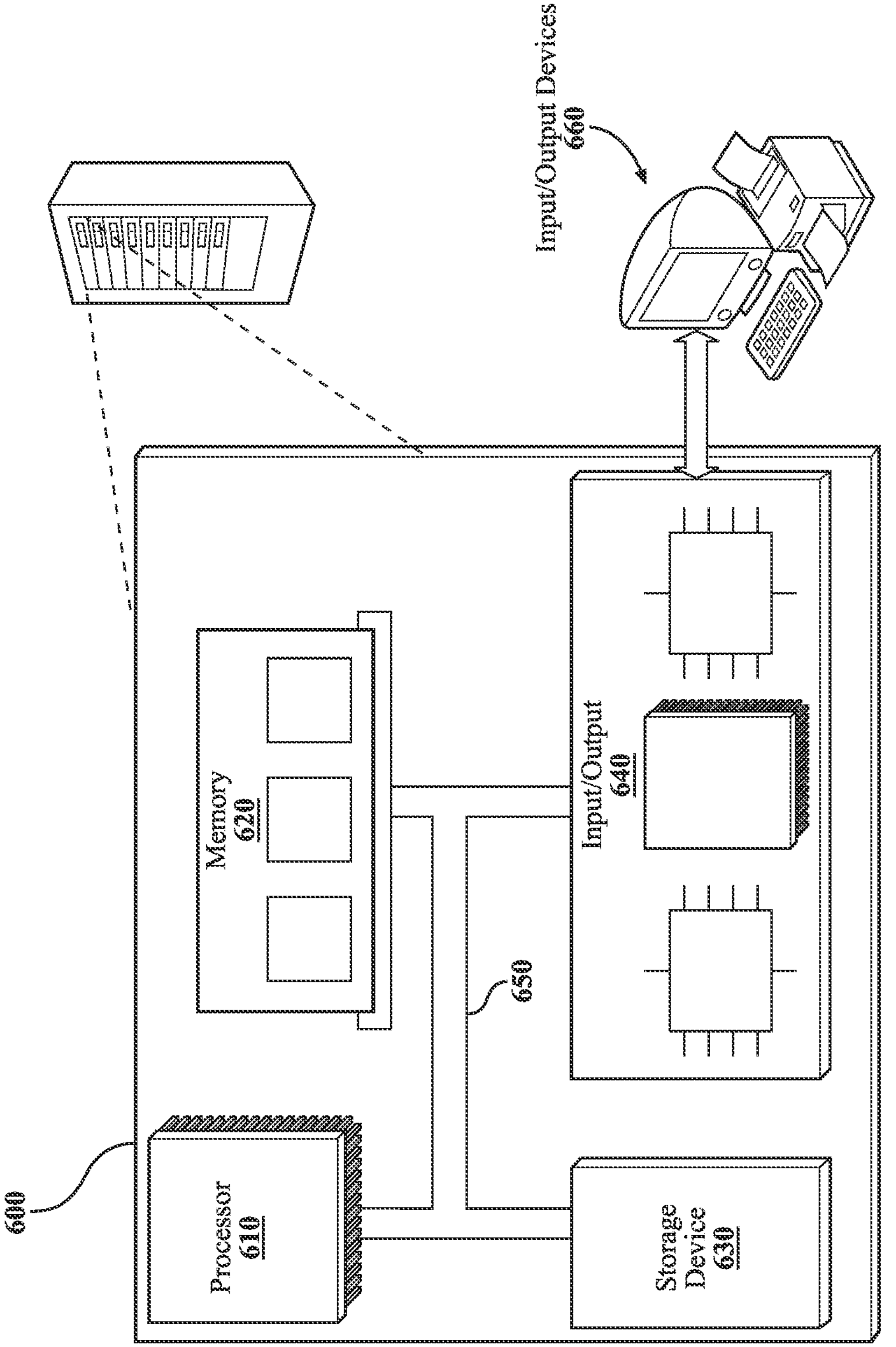
FIG. 6 is a block diagram of an example computer system that may be used in implementing the technology described in this document.

FIG. 6 is a block diagram of an example computer system 600 that may be used in implementing the technology described in this document (e.g., as part of controller 308). General-purpose computers, network appliances, mobile devices, or other electronic systems may also include at least portions of the system 600. The system 600 includes a processor 610, a memory 620, a storage device 630, and an input/output device 640. Each of the components 610, 620, 630, and 640 may be interconnected, for example, using a system bus 650. The processor 610 is capable of processing instructions for execution within the system 600. In some implementations, the processor 610 is a single-threaded processor. In some implementations, the processor 610 is a multi-threaded processor. The processor 610 is capable of processing instructions stored in the memory 620 or on the storage device 630.

The memory 620 stores information within the system 600. In some implementations, the memory 620 is a non-transitory computer-readable medium. In some implementations, the memory 620 is a volatile memory unit. In some implementations, the memory 620 is a non-volatile memory unit.

The storage device 630 is capable of providing mass storage for the system 600. In some implementations, the storage device 630 is a non-transitory computer-readable medium. In various different implementations, the storage device 630 may include, for example, a hard disk device, an optical disk device, a solid-date drive, a flash drive, or some other large capacity storage device. For example, the storage device may store long-term data (e.g., database data, file system data, etc.). The input/output device 640 provides input/output operations for the system 600. In some implementations, the input/output device 640 may include one or more of a network interface devices, e.g., an Ethernet card, a serial communication device, e.g., an RS-232 port, and/or a wireless interface device, e.g., an 802.11 card, a 3G wireless modem, or a 4G wireless modem. In some implementations, the input/output device may include driver devices configured to receive input data and send output data to other input/output devices, e.g., keyboard, printer and display devices 660. In some examples, mobile computing devices, mobile communication devices, and other devices may be used.

In some implementations, at least a portion of the approaches described above may be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 630 may be implemented in a distributed way over a network, for example as a server farm or a set of widely distributed servers, or may be implemented in a single computing device.

Although an example processing system has been described in FIG. 6, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of foregoing.

The term "system" may encompass all kinds of apparatus, devices, and machines for processing data, including by way of example a programmable processor, a computer, or multiple processors or computers. A processing system may include special purpose logic circuitry, e.g., a field programmable gate array (FPGA) or an application specific integrated circuit (ASIC). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA or an ASIC.

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a cathode ray tube (CRT) or liquid crystal display (LCD) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other.

According to an example, a waveguide for delivering light into the tissue of a subject may include a light entry portion, an extraction portion comprising a plurality of extraction features adapted to redirect light received from the light entry portion, and an NIR light emitting portion adapted to receive the light from the extraction portion and emit the light onto the tissue surface of the subject.

The the light entry portion may include an aspherical lens. The light entry portion may also include a light channel so that light entering the aspherical lens is dispersed and passes along the light channel to the extraction portion.

The plurality of extraction features may be at least three extraction features.

At least one outer surface of the waveguide may include a reflective coating or housing adjacent thereto. There may be a gap between the reflective coating or housing and the plurality of extraction features.

The extraction features are adapted to redirect (reflect) the light received from the light entry portion to a direction substantially perpendicular to the skin surface of the subject.

Each of the plurality of extraction features may include a surface oriented at an angle with respect to the direction normal to the skin surface. The angle may be in a range from 35 degrees to 75 degrees.

The NIR light emitting portion may, for example, be a flat shape or an arcuate shape having a concave lower surface. A concave lower surface may be adapted to conform to the skin surface of the subject. The concave lower profile may have a radius of curvature in a range from 3 cm to 10 cm.

The LDU or waveguide may include an integrated cooling system adapted to cool the skin surface of the subject. The integrated cooling system may be disposed within the emitting portion. Further, the integrated cooling system may include a fluidic channel(s) molded within the emitting portion and adapted to carry a coolant fluid (e.g., water). The fluidic channel(s) may have a serpentine shape. The serpentine shape may be defined by a plurality of substantially parallel conduits each connected by a bend, where the diameter of the inner surface of the substantially parallel conduits is greater than the diameter of the inner surface of the bends.

The fluidic channel(s) may occupy at least 20 percent of a surface area of the emitting portion.

At least a portion of the waveguide may be defined by a biocompatible, compliant material (e.g., silicone or optically clear silicone). The silicone material may have an elastic modulus in a range from 1 MPa to 50 MPa.

According to another example, a light treatment device for delivering light to a skin surface of a subject may include at least one support member adapted to retain at least one waveguide and position the at least one waveguide proximate the skin surface of the subject.

The support member may retain an array of waveguides and may be, for example, at least one of a strap, a cap, a helmet, or a combination thereof. Further, the support member may be adapted to position the at least one waveguide so as to avoid interaction between the emitted light and a predetermined region (e.g., venous sinus) of the subject.

The treatment device may also include a temperature measurement system for determining a temperature of the skin surface of the subject. The temperature measurement system may include, for example, a first probe for measuring a temperature of coolant fluid entering the waveguide via an inlet of the fluidic channel, a second probe for measuring a temperature of the coolant fluid exiting the waveguide at an outlet of the fluidic channel, and a reference probe for measuring a skin temperature at a non-treated location of the subject.

A light source of the treatment device may include at least one of a diode, a laser or a laser diode. The light source(s) may produce light having wavelengths of about 750 nm or about 940 nm, or wavelengths of 750 nm±30 nm and/or about 940 nm±30 nm.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

Terminology

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A near-infrared (NIR) light therapy device comprising:

at least one NIR light source to provide treatment NIR light; and a waveguide having i) a NIR light input surface where the treatment NIR light from the at least one NIR light source enters the waveguide and ii) a NIR light emitting surface where the treatment NIR light exits the waveguide, the waveguide comprising:

a lens feature forming the NIR light input surface and proximate the at least one NIR light source, the lens feature configured to at least substantially collimate the treatment NIR light from the at least one NIR light source and convey substantially collimated light in a first direction through the waveguide, a plurality of extractive surfaces on a surface of the waveguide and configured to reflect the substantially collimated light through the light emitting surface to a subject, wherein at least some of the extractive surfaces of the plurality of extractive surfaces is angled in a range of 35 to 75 degrees to a direction approximately normal to the subject, and wherein the plurality of extractive surfaces is configured to create a substantially uniform NIR light output across the light emitting surface, and at least one cooling channel configured to circulate a coolant that absorbs heat proximate to the NIR light emitting surface, wherein the waveguide is configured to transmit at least some reflected NIR light through the at least one cooling channel, and wherein the waveguide comprises silicone such that the lens feature, the plurality of extractive surfaces, the NIR light emitting surface, and the at least one cooling channel are comprised of silicone, and wherein the silicone is a low durometer silicone having a durometer in a range from 20 shore A to 80 shore A such that the NIR light emitting surface may at least partially conform to the subject.

2. The NIR light therapy device of claim 1 further comprising:

an inlet in the waveguide to receive the coolant prior to the coolant entering the at least one cooling channel;

a first temperature sensor configured to measure a first temperature of the coolant prior to the coolant entering the at least one cooling channel;

an outlet in the waveguide that conveys the coolant away from the waveguide after the coolant has travelled through the at least one cooling channel;

a second temperature sensor configured to measure a second temperature of the coolant after the coolant passes through the at least one cooling channel; and a control module to determine a difference between the first temperature and the second temperature.

3. The NIR light therapy device of claim 1 wherein the at least one coolant channel varies in diameter to slow coolant flow to increase heat exchange efficiency between the coolant and areas proximate to portions of the at least one cooling channel where the slowed coolant flows therethrough.

4. The NIR light therapy device of claim 1 wherein the at least one NIR light source produces light having wavelengths of approximately 750 nm and 940 nm, and wherein the light emitting surface is curved to conform to a surface of the subject.

5. The NIR light therapy device of claim 1 wherein at least some of the extractive surfaces of the plurality of extractive surfaces are angled at approximately 55 degrees to the direction approximately normal to the subject.

6. The NIR light therapy device of claim 1 further comprising:

at least one additional waveguide; and a support member configured to be applied to a head of the subject, the support member is further configured to at least:

retain the waveguide and the at least one additional waveguide; and ensure the treatment NIR light from each waveguide avoids a venous sinus region of the subject.

7. The NIR light therapy device of claim 1 further comprising a housing to house at least a portion of the waveguide, the housing comprises a reflective material to reflect treatment NIR light that exited the waveguide, in an area other than the light emitting surface, back into the waveguide.

8. A near-infrared (NIR) light therapy device comprising:

at least one optical light source to produce treatment NIR light; and a waveguide through which the treatment NIR light passes, the waveguide comprising:

a lens feature that receives and conveys the treatment NIR light to a first direction;

a plurality of extractive surfaces on a surface of the waveguide that receives the treatment NIR light travelling in the first direction and reflects the treatment NIR light in a direction that is substantially perpendicular to subject skin, wherein at least some of the extractive surfaces of the plurality of extractive surfaces are angled in a range of 35 to 75 degrees to a direction approximately normal to the subject skin;

a light emitting surface where the treatment NIR light reflected from the plurality of extractive surfaces passes therethrough to the subject skin, wherein the plurality of extractive surfaces is configured to create a substantially uniform NIR light output across the NIR light emitting surface; and at least one cooling channel configured to circulate a coolant that absorbs heat proximate to the light emitting surface, wherein the waveguide is configured to transmit at least some reflected treatment NIR light through the at least one cooling channel, wherein the waveguide comprises silicone such that the lens feature, the plurality of extractive surfaces, and the at least one cooling channel are comprised of silicone, and wherein the lens also collimates the NIR treatment light in the first direction.

9. The NIR light therapy device of claim 8 further comprising a control module configured to:

determine a temperature difference between a first temperature of the coolant prior to entering the at least one coolant channel and a second temperature of the coolant after the coolant has passed through the at least one cooling channel; and determine if the NIR therapy device is overheating the subject skin adjacent to the waveguide, wherein the overheating determination is based in part on the temperature difference.

10. The NIR light therapy device of claim 8 further comprising:

at least one additional waveguide; and a support member having the waveguide and the at least one additional waveguide coupled thereto, wherein the support member is configured to at least:

be applied to a head of the subject; and ensure the treatment NIR light from each waveguide avoids a venous sinus region of the subject.

11. A method of manufacturing a near-infrared (NIR) light therapy device to treat a subject comprising:

forming a waveguide, wherein forming the waveguide comprises:

molding a lens into the waveguide, the lens configured to receive NIR treatment light from a NIR light source and convey the NIR treatment light in a first direction, wherein the waveguide is comprised of an optically clear low durometer silicone and the lens is further configured to collimate the NIR treatment light in the first direction, and wherein the optically clear low durometer silicone has a durometer in a range from 20 shore A to 80 shore A such that the NIR light emitting surface may at least partially conform to the subject;

molding an elongated portion of the waveguide where the conveyed NIR treatment light propagates therethrough in substantially the first direction;

molding an extractive portion onto a surface of the waveguide, the extractive portion configured to reflect the NIR treatment light traveling in the first direction to create reflected NIR treatment light propagating in a direction that is substantially perpendicular to the subject;

molding a NIR light emitting surface onto the waveguide, wherein the waveguide is configured to pass the reflected NIR treatment light out of the waveguide to the subject via the NIR light emitting surface, wherein the extractive portion is configured to create a substantially uniform NIR light output across the NIR light emitting surface; and molding at least one cooling channel proximate to the NIR light emitting surface, the cooling channel configured to:

pass the reflected NIR light therethrough; and circulate a coolant that absorbs heat that is proximate to the NIR light emitting surface.

12. The method of claim 11 further comprising:

creating a first temperature sensor affixable to the NIR light therapy device, the first temperature sensor configured to measure a first temperature of the coolant prior to the coolant entering the at least one cooling channel;

creating a second temperature sensor affixable to the NIR light therapy device, the second temperature sensor configured to measure a second temperature of the coolant after the coolant passes through the at least one cooling channel; and creating a control module affixable to the NIR light therapy device, the control module configured to determine a difference between the first temperature and the second temperature.

13. The method of claim 12 further comprising:

forming at least one additional waveguide; and positioning the waveguide and the at least one additional waveguide on a wearable support member such that, when the wearable support member is applied to a head of the subject, reflected NIR treatment light from each waveguide avoids a venous sinus region of the subject.

14. The method of claim 11 further comprising attaching a reflective housing to at least a portion of the waveguide, the reflective housing configured to reflect light that exits the waveguide from an area other than the NIR light emitting surface back into the waveguide.

15. A near-infrared (NIR) light therapy device comprising:

at least one NIR light source to provide treatment NIR light, a control module; and a waveguide having i) a NIR light input surface where the treatment NIR light from the at least one NIR light source enters the waveguide and ii) a NIR light emitting surface where the treatment NIR light exits the waveguide, the waveguide comprising:

a lens feature forming the NIR light input surface and proximate the at least one NIR light source, the lens feature configured to at least substantially collimate the treatment NIR light from the at least one NIR light source and convey substantially collimated light in a first direction through the waveguide, a plurality of extractive surfaces on a surface of the waveguide and configured to reflect the substantially collimated light through the light emitting surface to a subject, wherein at least some of the extractive surfaces of the plurality of extractive surfaces is angled in a range of 35 to 75 degrees to a direction approximately normal to the subject, and wherein the plurality of extractive surfaces is configured to create a substantially uniform NIR light output across the light emitting surface, at least one cooling channel configured to circulate a coolant that absorbs heat proximate to the NIR light emitting surface, wherein the waveguide is configured to transmit at least some reflected NIR light through the at least one cooling channel;

an inlet in the waveguide to receive the coolant prior to the coolant entering the at least one cooling channel, a first temperature sensor configured to measure a first temperature of the coolant prior to the coolant entering the at least one cooling channel, an outlet in the waveguide that conveys the coolant away from the waveguide after the coolant has travelled through the at least one cooling channel, and a second temperature sensor configured to measure a second temperature of the coolant after the coolant passes through the at least one cooling channel, wherein the control module is configured to determine a difference between the first temperature and the second temperature.

16. A near-infrared (NIR) light therapy device comprising:

at least one NIR light source to provide treatment NIR light;

a support member configured to be applied to a head of a subject;

a waveguide having i) a NIR light input surface where the treatment NIR light from the at least one NIR light source enters the waveguide and ii) a NIR light emitting surface where the treatment NIR light exits the waveguide, the waveguide comprising:

a lens feature forming the NIR light input surface and proximate the at least one NIR light source, the lens feature configured to at least substantially collimate the treatment NIR light from the at least one NIR light source and convey substantially collimated light in a first direction through the waveguide, a plurality of extractive surfaces on a surface of the waveguide and configured to reflect the substantially collimated light through the light emitting surface to the subject, wherein at least some of the extractive surfaces of the plurality of extractive surfaces is angled in a range of 35 to 75 degrees to a direction approximately normal to the subject, and wherein the plurality of extractive surfaces is configured to create a substantially uniform NIR light output across the light emitting surface, and at least one additional waveguide, wherein the support member is configured to at least i) retain the waveguide and the at least one additional waveguide and ii) ensure the treatment NIR light from each waveguide avoids a venous sinus region of the subject.

* * * * *